United States Patent
Levy et al.

(10) Patent No.: US 8,926,502 B2
(45) Date of Patent: Jan. 6, 2015

(54) MULTI CAMERA ENDOSCOPE HAVING A SIDE SERVICE CHANNEL

(75) Inventors: Avi Levy, Herzliya (IL); Moshe Levi, Gane Tikva (IL)

(73) Assignee: EndoChoice, Inc., Alpharetta, GA (US)

( * ) Notice: Subject to any disclaimer, the term of this patent is extended or adjusted under 35 U.S.C. 154(b) by 0 days.

(21) Appl. No.: 13/413,141

(22) Filed: Mar. 6, 2012

(65) Prior Publication Data

US 2012/0232340 A1   Sep. 13, 2012

Related U.S. Application Data

(60) Provisional application No. 61/449,743, filed on Mar. 7, 2011.

(51) Int. Cl.
*A61B 1/04* (2006.01)
*A61B 1/00* (2006.01)
*A61B 1/06* (2006.01)
*A61B 1/015* (2006.01)
*A61B 1/018* (2006.01)

(52) U.S. Cl.
CPC .......... *A61B 1/00177* (2013.01); *A61B 1/00181* (2013.01); *A61B 1/015* (2013.01); *A61B 1/018* (2013.01); *A61B 1/0615* (2013.01); *A61B 1/00091* (2013.01)
USPC ........... 600/170; 600/127; 600/129; 600/153; 600/171

(58) Field of Classification Search
CPC ........... A61B 1/00089; A61B 1/00091; A61B 1/00094; A61B 1/00096; A61B 1/00098; A61B 1/00101; A61B 1/00137; A61B 1/00163; A61B 1/00174; A61B 1/00177; A61B 1/00179; A61B 1/00181; A61B 1/00183; A61B 1/00188; A61B 1/00193; A61B 1/0019; A61B 1/012; A61B 1/015; A61B 1/018; A61B 1/0125; A61B 1/06; A61B 1/0607; A61B 1/0615; A61B 1/0623; A61B 1/0661; A61B 1/0676; A61B 1/0684; A61B 1/12; A61B 1/127; A61B 1/00087; G01N 21/954; G02B 23/2476
USPC ......... 600/104, 106, 107, 109–116, 153, 157, 600/158, 160–182, 127, 129; 356/241.1–241.6; 385/117
See application file for complete search history.

(56) References Cited

U.S. PATENT DOCUMENTS 4,253,448 A   3/1981   Terada
4,261,345 A   4/1981   Yamaguchi
(Continued)

FOREIGN PATENT DOCUMENTS

CN   201108422 Y   9/2008
DE   102005008153 A1   11/2005
(Continued)

OTHER PUBLICATIONS

International Search Report of PCT/IL10/00476 mailed Sep. 27, 2010, 2 pages.
(Continued)

*Primary Examiner* — Ryan Henderson
(74) *Attorney, Agent, or Firm* — Novel IP

(57) ABSTRACT

There is provided herein an endoscope assembly comprising at least one front-pointing camera and at least one front illuminator associated therewith, at least one side-pointing camera and at least one of side illuminator associated therewith, a front working channel configured for insertion of a medical tool and a side service channel configured for insertion of a medical tool.

34 Claims, 10 Drawing Sheets

(56) References Cited

U.S. PATENT DOCUMENTS

| | | |
|---|---|---|
| 4,402,313 A | 9/1983 | Yabe |
| 4,414,608 A | 11/1983 | Furihata |
| 4,439,030 A | 3/1984 | Ueda |
| 4,469,090 A | 9/1984 | Konomura |
| 4,522,196 A | 6/1985 | Cunningham |
| 4,565,423 A | 1/1986 | Ueda |
| 4,576,144 A | 3/1986 | Ishii |
| 4,590,923 A | 5/1986 | Watanabe |
| 4,699,463 A | 10/1987 | D'Amelio |
| 4,708,126 A | 11/1987 | Toda |
| 4,736,732 A | 4/1988 | Shimonaka |
| 4,753,222 A | 6/1988 | Morishita |
| 4,794,913 A | 1/1989 | Shimonaka |
| 4,846,154 A | 7/1989 | MacAnally |
| 4,878,485 A | 11/1989 | Adair |
| 4,888,639 A | 12/1989 | Yabe |
| 4,905,670 A | 3/1990 | Adair |
| 4,914,521 A | 4/1990 | Adair |
| 4,974,075 A | 11/1990 | Nakajima |
| 4,982,724 A | 1/1991 | Saito |
| 4,998,182 A | 3/1991 | Krauter |
| 5,166,787 A | 11/1992 | Irion |
| 5,239,983 A | 8/1993 | Katsurada |
| 5,296,971 A | 3/1994 | Mori |
| 5,299,561 A | 4/1994 | Yoshimoto |
| 5,305,121 A | 4/1994 | Moll |
| 5,313,934 A | 5/1994 | Wiita |
| 5,339,800 A | 8/1994 | Wiita |
| 5,359,456 A | 10/1994 | Kikuchi |
| 5,398,056 A | 3/1995 | Yabe |
| 5,452,391 A | 9/1995 | Chou |
| 5,507,717 A | 4/1996 | Kura |
| 5,518,502 A | 5/1996 | Kaplan |
| 5,547,455 A | 8/1996 | McKenna |
| 5,589,874 A | 12/1996 | Buchin |
| 5,609,560 A | 3/1997 | Ichikawa |
| 5,653,677 A | 8/1997 | Okada |
| 5,656,011 A | 8/1997 | Uihlein |
| 5,679,110 A | 10/1997 | Hamazaki |
| 5,685,823 A | 11/1997 | Ito |
| 5,701,155 A | 12/1997 | Wood |
| 5,702,345 A | 12/1997 | Wood |
| 5,716,323 A | 2/1998 | Lee |
| 5,725,476 A | 3/1998 | Yasui |
| 5,782,751 A | 7/1998 | Matsuno |
| 5,800,341 A | 9/1998 | McKenna |
| 5,830,124 A | 11/1998 | Suzuki |
| 5,871,439 A | 2/1999 | Takahashi |
| 5,876,326 A | 3/1999 | Takamura |
| 5,913,817 A | 6/1999 | Lee |
| 5,914,810 A | 6/1999 | Watts |
| 5,929,901 A | 7/1999 | Adair |
| 5,930,424 A | 7/1999 | Heimberger |
| 5,940,126 A * | 8/1999 | Kimura ........................ 348/294 |
| 5,961,445 A | 10/1999 | Chikama |
| 5,986,693 A | 11/1999 | Adair |
| 5,989,185 A | 11/1999 | Miyazaki |
| 6,009,189 A | 12/1999 | Schaack |
| 6,043,839 A | 3/2000 | Adair |
| 6,080,104 A | 6/2000 | Ozawa |
| 6,110,127 A | 8/2000 | Suzuki |
| 6,139,490 A | 10/2000 | Breidenthal |
| 6,184,923 B1 | 2/2001 | Miyazaki |
| 6,211,904 B1 | 4/2001 | Adair |
| 6,215,517 B1 | 4/2001 | Takahashi |
| 6,217,500 B1 | 4/2001 | Helseth |
| 6,245,086 B1 | 6/2001 | Storz |
| 6,261,226 B1 | 7/2001 | McKenna |
| 6,275,255 B1 | 8/2001 | Adair |
| 6,306,082 B1 | 10/2001 | Takahashi |
| 6,310,642 B1 | 10/2001 | Adair |
| 6,315,712 B1 | 11/2001 | Rovegno |
| 6,322,496 B1 | 11/2001 | Iida |
| 6,387,045 B1 | 5/2002 | Takahashi |
| 6,422,995 B2 | 7/2002 | Akiba |
| 6,450,950 B2 | 9/2002 | Irion |
| 6,461,304 B1 | 10/2002 | Tanaka |
| 6,464,631 B1 | 10/2002 | Girke |
| 6,464,633 B1 | 10/2002 | Hosoda |
| 6,468,201 B1 | 10/2002 | Burdick |
| 6,468,202 B1 | 10/2002 | Irion |
| 6,471,636 B1 | 10/2002 | Sano |
| 6,471,637 B1 | 10/2002 | Green |
| 6,473,116 B1 | 10/2002 | Takahashi |
| 6,500,115 B2 | 12/2002 | Krattiger |
| 6,514,210 B2 | 2/2003 | Ohara |
| 6,520,908 B1 | 2/2003 | Ikeda |
| 6,527,704 B1 | 3/2003 | Chang |
| 6,533,722 B2 | 3/2003 | Nakashima |
| 6,554,767 B2 | 4/2003 | Tanaka |
| 6,569,084 B1 | 5/2003 | Mizuno |
| 6,582,361 B2 | 6/2003 | Hirano |
| 6,589,168 B2 | 7/2003 | Thompson |
| 6,606,113 B2 | 8/2003 | Nakamura |
| D481,125 S | 10/2003 | Hayamizu |
| 6,638,212 B1 | 10/2003 | Oshima |
| 6,638,214 B2 | 10/2003 | Akiba |
| 6,641,531 B2 | 11/2003 | Kehr |
| 6,656,111 B2 | 12/2003 | Fujii |
| 6,671,099 B2 | 12/2003 | Nagata |
| 6,692,430 B2 | 2/2004 | Adler |
| 6,692,431 B2 | 2/2004 | Kazakevich |
| 6,699,181 B2 | 3/2004 | Wako |
| 6,712,760 B2 | 3/2004 | Sano |
| D490,898 S | 6/2004 | Hayamizu |
| 6,764,439 B2 | 7/2004 | Schaaf |
| 6,793,621 B2 | 9/2004 | Butler |
| 6,801,325 B2 | 10/2004 | Farr |
| 6,832,984 B2 * | 12/2004 | Stelzer et al. ................. 600/106 |
| 6,846,311 B2 | 1/2005 | Gatto |
| 6,849,043 B2 | 2/2005 | Kondo |
| 6,876,380 B2 | 4/2005 | Abe |
| 6,887,194 B2 | 5/2005 | Hart |
| 6,888,119 B2 | 5/2005 | Iizuka |
| 6,898,086 B2 | 5/2005 | Takami |
| 6,899,673 B2 | 5/2005 | Ogura |
| 6,900,950 B2 | 5/2005 | Nagata |
| 6,902,529 B2 | 6/2005 | Onishi |
| 6,921,362 B2 | 7/2005 | Ouchi |
| 6,930,705 B2 | 8/2005 | Tanaka |
| 6,943,821 B2 | 9/2005 | Abe |
| 6,944,031 B2 | 9/2005 | Takami |
| 6,945,929 B2 | 9/2005 | Ando |
| 6,947,070 B2 | 9/2005 | Takami |
| 6,950,691 B2 | 9/2005 | Uchikubo |
| 6,982,740 B2 | 1/2006 | Adair |
| 6,997,871 B2 | 2/2006 | Sonnenschein |
| 7,030,904 B2 | 4/2006 | Adair |
| 7,074,181 B2 | 7/2006 | Futatsugi |
| 7,074,182 B2 | 7/2006 | Rovegno |
| 7,097,615 B2 | 8/2006 | Banik |
| 7,104,951 B2 | 9/2006 | Hasegawa |
| 7,108,656 B2 | 9/2006 | Fujikawa |
| 7,108,657 B2 | 9/2006 | Irion |
| 7,128,709 B2 | 10/2006 | Saruya |
| 7,133,063 B2 | 11/2006 | Abe |
| D534,656 S | 1/2007 | Pilvisto |
| 7,156,863 B2 | 1/2007 | Sonnenschein |
| 7,223,231 B2 | 5/2007 | Akiba |
| 7,231,135 B2 | 6/2007 | Esenyan |
| 7,233,820 B2 | 6/2007 | Gilboa |
| 7,242,833 B2 | 7/2007 | Yang |
| 7,248,281 B2 | 7/2007 | Abe |
| 7,252,633 B2 | 8/2007 | Obata |
| 7,255,676 B2 | 8/2007 | Higuchi |
| 7,262,797 B2 | 8/2007 | Weldum |
| 7,267,647 B2 | 9/2007 | Okada |
| 7,273,452 B2 | 9/2007 | Barbato |
| 7,277,120 B2 | 10/2007 | Gere |
| 7,282,025 B2 | 10/2007 | Abe |
| 7,306,588 B2 | 12/2007 | Loeb |
| 7,330,749 B1 | 2/2008 | Bhunachet |
| D564,659 S | 3/2008 | Hayashi |
| D564,660 S | 3/2008 | Hayashi |

(56) References Cited

U.S. PATENT DOCUMENTS

| | | |
|---|---|---|
| 7,351,202 B2 | 4/2008 | Long |
| 7,355,625 B1 | 4/2008 | Mochida |
| 7,358,987 B2 | 4/2008 | Takeshige |
| 7,365,768 B1 | 4/2008 | Ono |
| 7,371,211 B2 | 5/2008 | Akiba |
| 7,384,308 B2 | 6/2008 | Boehnlein |
| 7,399,304 B2 | 7/2008 | Gambale |
| 7,400,341 B2 | 7/2008 | Abe |
| 7,420,586 B2 | 9/2008 | Higuchi |
| 7,431,619 B2 | 10/2008 | Boehnlein |
| 7,435,217 B2 | 10/2008 | Wiklof |
| 7,440,005 B2 | 10/2008 | Enomoto |
| 7,484,709 B2 | 2/2009 | Efinger |
| 7,492,388 B2 | 2/2009 | Odlivak |
| 7,518,632 B2 | 4/2009 | Konomura |
| 7,530,948 B2 | 5/2009 | Seibel |
| 7,553,276 B2 | 6/2009 | Iddan |
| 7,559,892 B2 | 7/2009 | Adler |
| 7,569,012 B2 | 8/2009 | Tanaka |
| 7,581,988 B2 | 9/2009 | Boehnlein |
| 7,582,055 B2 | 9/2009 | Komiya |
| 7,582,056 B2 | 9/2009 | Noguchi |
| 7,584,534 B2 | 9/2009 | Pease |
| 7,585,274 B2 | 9/2009 | Homma |
| 7,588,535 B2 | 9/2009 | Adler |
| 7,593,051 B2 | 9/2009 | Suda |
| 7,621,868 B2 | 11/2009 | Breidenthal |
| 7,621,869 B2 | 11/2009 | Ratnakar |
| 7,695,429 B2 | 4/2010 | Hino |
| 7,699,772 B2 | 4/2010 | Pauker |
| 7,749,156 B2 | 7/2010 | Ouchi |
| 7,749,159 B2 | 7/2010 | Crowley |
| 7,758,495 B2 | 7/2010 | Pease |
| 7,758,499 B2 | 7/2010 | Adler |
| 7,773,122 B2 | 8/2010 | Irion |
| 7,775,971 B2 | 8/2010 | Fujimori |
| 7,775,973 B2 | 8/2010 | Okada |
| 7,789,822 B2 | 9/2010 | Suzuki |
| RE41,807 E | 10/2010 | Yokoi |
| 7,821,529 B2 | 10/2010 | Mochida |
| 7,837,614 B2 | 11/2010 | Segawa |
| 7,841,880 B2 | 11/2010 | Ikeda |
| 7,846,090 B2 | 12/2010 | Pilvisto |
| 7,893,956 B2 | 2/2011 | Ayrenschmalz |
| 7,896,802 B2 | 3/2011 | Otawara |
| 7,901,352 B2 | 3/2011 | Minami |
| 7,907,168 B2 | 3/2011 | Eino |
| 7,914,443 B2 | 3/2011 | Uchimura |
| 7,918,788 B2 | 4/2011 | Lin |
| 7,938,773 B2 | 5/2011 | Kawai |
| 7,942,814 B2 | 5/2011 | Remijan |
| 7,951,068 B2 | 5/2011 | Kura |
| 7,967,745 B2 | 6/2011 | Gilad |
| 7,976,462 B2 | 7/2011 | Wright |
| 7,995,093 B2 | 8/2011 | Takeuchi |
| 7,998,064 B2 | 8/2011 | Otawara |
| 8,002,696 B2 | 8/2011 | Suzuki |
| 8,033,992 B2 | 10/2011 | Hino |
| 8,038,600 B2 | 10/2011 | Uchiyama |
| 8,043,207 B2 | 10/2011 | Adams |
| 8,060,172 B2 | 11/2011 | Ishihara |
| 8,066,631 B2 | 11/2011 | Wimmer |
| 8,072,537 B2 | 12/2011 | Schwarz |
| 8,075,477 B2 | 12/2011 | Nakamura |
| 8,075,478 B2 | 12/2011 | Campos |
| 8,100,920 B2 | 1/2012 | Gambale |
| 8,105,233 B2 | 1/2012 | AbouElKheir |
| 8,113,846 B2 | 2/2012 | Wallaker |
| 8,125,515 B2 | 2/2012 | Hibi |
| 8,135,454 B2 | 3/2012 | Daniels |
| 8,152,718 B2 | 4/2012 | Cheng |
| 8,152,821 B2 | 4/2012 | Gambale |
| 8,157,798 B2 | 4/2012 | Takahashi |
| 8,167,791 B2 | 5/2012 | Tanaka |
| 8,167,796 B2 | 5/2012 | Negishi |
| 8,182,419 B2 | 5/2012 | Kohno |
| 8,187,171 B2 | 5/2012 | Irion |
| 8,187,174 B2 | 5/2012 | Wang |
| 8,189,062 B2 | 5/2012 | Irion |
| 8,194,380 B2 | 6/2012 | Murata |
| 8,197,400 B2 | 6/2012 | Boutillette |
| 8,208,015 B2 | 6/2012 | Unsai |
| 8,211,009 B2 | 7/2012 | Tanaka |
| 8,221,311 B2 | 7/2012 | Campos |
| 8,228,369 B2 | 7/2012 | Kojima |
| 8,229,549 B2 | 7/2012 | Whitman |
| 8,235,942 B2 | 8/2012 | Frassica |
| 8,248,414 B2 | 8/2012 | Gattani |
| 8,262,565 B2 | 9/2012 | Okada |
| 8,279,275 B2 | 10/2012 | Gono |
| 8,295,566 B2 | 10/2012 | Nishimura |
| 8,310,529 B2 | 11/2012 | Krupnick |
| 8,334,900 B2 | 12/2012 | Qu |
| 8,345,092 B2 | 1/2013 | Takasaki |
| 8,348,835 B2 | 1/2013 | Fujimori |
| 8,360,960 B2 | 1/2013 | Sasaki |
| 8,360,964 B2 | 1/2013 | Ertas |
| 8,366,623 B2 | 2/2013 | Misono |
| 8,382,673 B2 | 2/2013 | Nagano |
| 8,394,013 B2 | 3/2013 | Ichimura |
| 8,394,014 B2 | 3/2013 | Fuerst |
| 8,425,405 B2 | 4/2013 | Mitani |
| 8,435,173 B2 | 5/2013 | Hosaka |
| 8,439,829 B2 | 5/2013 | Miyamoto |
| 8,444,547 B2 | 5/2013 | Miyamoto |
| 8,444,548 B2 | 5/2013 | Kumei |
| 8,449,456 B2 | 5/2013 | Ueno |
| 8,456,562 B2 | 6/2013 | Ishii |
| 8,460,182 B2 | 6/2013 | Ouyang |
| 8,465,421 B2 | 6/2013 | Finkman |
| 8,480,670 B2 | 7/2013 | Sugita |
| 8,491,467 B2 | 7/2013 | Miyamoto |
| 8,520,919 B2 | 8/2013 | Stepp |
| 8,523,764 B2 | 9/2013 | Hatcher |
| 8,523,766 B2 | 9/2013 | Kudoh |
| 2002/0007110 A1 | 1/2002 | Irion |
| 2002/0087047 A1 | 7/2002 | Remijan |
| 2002/0098732 A1 | 7/2002 | Shimizu |
| 2002/0109774 A1 | 8/2002 | Meron |
| 2002/0151768 A1 | 10/2002 | Akiba |
| 2002/0161282 A1 | 10/2002 | Fulghum |
| 2002/0183591 A1 | 12/2002 | Matsuura |
| 2003/0032860 A1 | 2/2003 | Avni |
| 2003/0036681 A1 | 2/2003 | Aviv |
| 2003/0055314 A1 | 3/2003 | Petitto |
| 2003/0125788 A1 | 7/2003 | Long |
| 2003/0139648 A1 | 7/2003 | Foley |
| 2003/0181787 A1 | 9/2003 | Kondo |
| 2003/0199860 A1 | 10/2003 | Loeb |
| 2004/0015049 A1 | 1/2004 | Zaar |
| 2004/0019347 A1 | 1/2004 | Sakurai |
| 2004/0024290 A1 | 2/2004 | Root |
| 2004/0034311 A1 | 2/2004 | Mihalcik |
| 2004/0073120 A1 | 4/2004 | Motz |
| 2004/0104999 A1 | 6/2004 | Okada |
| 2004/0111012 A1 | 6/2004 | Whitman |
| 2004/0133076 A1 | 7/2004 | Kobayashi |
| 2004/0143162 A1 | 7/2004 | Krattiger |
| 2004/0158129 A1* | 8/2004 | Okada et al. ............ 600/168 |
| 2004/0160682 A1 | 8/2004 | Miyano |
| 2004/0176661 A1 | 9/2004 | Futatsugi |
| 2004/0210113 A1 | 10/2004 | Hasegawa |
| 2004/0220451 A1 | 11/2004 | Gravenstein |
| 2004/0242958 A1 | 12/2004 | Fujikawa |
| 2004/0242961 A1 | 12/2004 | Bughici |
| 2004/0254423 A1 | 12/2004 | Wendlandt |
| 2004/0267093 A1 | 12/2004 | Miyagi |
| 2005/0020876 A1 | 1/2005 | Shioda |
| 2005/0027164 A1 | 2/2005 | Barbato |
| 2005/0038317 A1 | 2/2005 | Ratnakar |
| 2005/0038318 A1 | 2/2005 | Goldwasser |
| 2005/0043583 A1 | 2/2005 | Killmann |
| 2005/0080342 A1 | 4/2005 | Gilreath |
| 2005/0090709 A1* | 4/2005 | Okada et al. ............ 600/104 |

(56) References Cited

U.S. PATENT DOCUMENTS

| | | | |
|---|---|---|---|
| 2005/0096501 A1 | 5/2005 | Stelzer | |
| 2005/0154255 A1 | 7/2005 | Jacobs | |
| 2005/0154262 A1 | 7/2005 | Banik | |
| 2005/0182295 A1 | 8/2005 | Soper | |
| 2005/0203338 A1 | 9/2005 | Couvillon | |
| 2005/0234296 A1 | 10/2005 | Saadat | |
| 2005/0261553 A1 | 11/2005 | Swain | |
| 2005/0272975 A1 | 12/2005 | McWeeney | |
| 2005/0284491 A1 | 12/2005 | Tashiro | |
| 2006/0052663 A1 | 3/2006 | Koitabashi | |
| 2006/0063976 A1 | 3/2006 | Aizenfeld | |
| 2006/0069307 A1 | 3/2006 | Boulais | |
| 2006/0069314 A1 | 3/2006 | Farr | |
| 2006/0149129 A1 | 7/2006 | Watts | |
| 2006/0173244 A1 | 8/2006 | Boulais | |
| 2006/0183971 A1 | 8/2006 | Haviv | |
| 2006/0183975 A1* | 8/2006 | Saadat et al. | 600/139 |
| 2006/0189845 A1 | 8/2006 | Maahs | |
| 2006/0211916 A1 | 9/2006 | Kasahara | |
| 2006/0217594 A1 | 9/2006 | Ferguson | |
| 2006/0224040 A1 | 10/2006 | Khait | |
| 2006/0229499 A1 | 10/2006 | Eisenkolb | |
| 2006/0241347 A1 | 10/2006 | Whitehead | |
| 2006/0264704 A1 | 11/2006 | Fujimori | |
| 2006/0293556 A1 | 12/2006 | Garner | |
| 2006/0293562 A1 | 12/2006 | Uchimura | |
| 2007/0015964 A1 | 1/2007 | Eversull | |
| 2007/0015968 A1 | 1/2007 | Shelnutt | |
| 2007/0019916 A1 | 1/2007 | Takami | |
| 2007/0073109 A1 | 3/2007 | Irion | |
| 2007/0078304 A1 | 4/2007 | Shimizu | |
| 2007/0083081 A1 | 4/2007 | Schlagenhauf | |
| 2007/0100206 A1 | 5/2007 | Lin | |
| 2007/0115376 A1 | 5/2007 | Igarashi | |
| 2007/0118019 A1 | 5/2007 | Mitani | |
| 2007/0123748 A1 | 5/2007 | Meglan | |
| 2007/0142711 A1 | 6/2007 | Bayer | |
| 2007/0167673 A1 | 7/2007 | Enomoto | |
| 2007/0173686 A1 | 7/2007 | Lin | |
| 2007/0173687 A1 | 7/2007 | Shima | |
| 2007/0177008 A1 | 8/2007 | Bayer | |
| 2007/0177009 A1 | 8/2007 | Bayer | |
| 2007/0185384 A1 | 8/2007 | Bayer | |
| 2007/0203396 A1 | 8/2007 | McCutcheon | |
| 2007/0206945 A1 | 9/2007 | DeLorme | |
| 2007/0208225 A1 | 9/2007 | Czaniera | |
| 2007/0213590 A1 | 9/2007 | Squicciarini | |
| 2007/0225556 A1 | 9/2007 | Ortiz | |
| 2007/0225565 A1 | 9/2007 | Ogino | |
| 2007/0229656 A1 | 10/2007 | Khait | |
| 2007/0244353 A1 | 10/2007 | Larsen | |
| 2007/0244362 A1 | 10/2007 | El-Hachem | |
| 2007/0244366 A1 | 10/2007 | Murata | |
| 2007/0249899 A1 | 10/2007 | Seifert | |
| 2007/0265498 A1 | 11/2007 | Ito | |
| 2007/0282165 A1 | 12/2007 | Hopkins | |
| 2007/0293720 A1 | 12/2007 | Bayer | |
| 2008/0009672 A1 | 1/2008 | Krattiger | |
| 2008/0021274 A1 | 1/2008 | Bayer | |
| 2008/0021281 A1 | 1/2008 | Fujimori | |
| 2008/0039689 A1 | 2/2008 | Yoshimitsu | |
| 2008/0039693 A1 | 2/2008 | Karasawa | |
| 2008/0045797 A1 | 2/2008 | Yasushi | |
| 2008/0051628 A1 | 2/2008 | Pecherer | |
| 2008/0051629 A1 | 2/2008 | Sugiyama | |
| 2008/0051655 A1 | 2/2008 | Sato | |
| 2008/0058595 A1 | 3/2008 | Snoke | |
| 2008/0058598 A1 | 3/2008 | Ries | |
| 2008/0058601 A1 | 3/2008 | Fujimori | |
| 2008/0064931 A1 | 3/2008 | Schena | |
| 2008/0065127 A1 | 3/2008 | Adams | |
| 2008/0071290 A1* | 3/2008 | Larkin et al. | 606/130 |
| 2008/0100699 A1 | 5/2008 | Hibi | |
| 2008/0130108 A1 | 6/2008 | Bayer | |
| 2008/0139881 A1 | 6/2008 | Cover | |
| 2008/0167529 A1* | 7/2008 | Otawara | 600/168 |
| 2008/0171910 A1 | 7/2008 | Kanazawa | |
| 2008/0177139 A1 | 7/2008 | Courtney | |
| 2008/0177140 A1 | 7/2008 | Cline | |
| 2008/0188715 A1 | 8/2008 | Fujimoto | |
| 2008/0225134 A1 | 9/2008 | Amling | |
| 2008/0255425 A1 | 10/2008 | Voegele | |
| 2008/0262302 A1 | 10/2008 | Azarbarzin | |
| 2008/0262312 A1 | 10/2008 | Carroll | |
| 2008/0312497 A1 | 12/2008 | Elmouelhi | |
| 2009/0054790 A1 | 2/2009 | Czaniera | |
| 2009/0093679 A1 | 4/2009 | Suigetsu | |
| 2009/0118577 A9 | 5/2009 | Snay | |
| 2009/0137869 A1 | 5/2009 | Soutorine | |
| 2009/0147076 A1 | 6/2009 | Ertas | |
| 2009/0163769 A1 | 6/2009 | Robertson | |
| 2009/0209811 A1 | 8/2009 | Higuchi | |
| 2009/0216084 A1 | 8/2009 | Yamane | |
| 2009/0231419 A1 | 9/2009 | Bayer | |
| 2009/0247831 A1 | 10/2009 | Miyamoto | |
| 2009/0253966 A1 | 10/2009 | Ichimura | |
| 2009/0259097 A1 | 10/2009 | Thompson | |
| 2009/0259102 A1 | 10/2009 | Koninckx | |
| 2009/0268011 A1 | 10/2009 | Scott | |
| 2009/0284649 A1 | 11/2009 | Pease | |
| 2009/0287047 A1 | 11/2009 | Onoda | |
| 2009/0306474 A1 | 12/2009 | Wilson | |
| 2009/0306476 A1 | 12/2009 | Banik | |
| 2009/0318757 A1 | 12/2009 | Singh | |
| 2010/0010301 A1 | 1/2010 | Hale | |
| 2010/0010302 A1 | 1/2010 | Hadani | |
| 2010/0016673 A1 | 1/2010 | Bandy | |
| 2010/0030020 A1 | 2/2010 | Sanders | |
| 2010/0042097 A1 | 2/2010 | Newton | |
| 2010/0047733 A1 | 2/2010 | Nahlieli | |
| 2010/0053312 A1 | 3/2010 | Watanabe | |
| 2010/0073470 A1 | 3/2010 | Takasaki | |
| 2010/0076268 A1 | 3/2010 | Takasugi | |
| 2010/0081874 A1 | 4/2010 | Miyamoto | |
| 2010/0081875 A1 | 4/2010 | Fowler | |
| 2010/0087706 A1 | 4/2010 | Syed | |
| 2010/0121142 A1 | 5/2010 | Ouyang | |
| 2010/0130822 A1 | 5/2010 | Katayama | |
| 2010/0137682 A1 | 6/2010 | Doguchi | |
| 2010/0137687 A1 | 6/2010 | Schwartz | |
| 2010/0141746 A1 | 6/2010 | Ikeda | |
| 2010/0152612 A1 | 6/2010 | Headley | |
| 2010/0160729 A1* | 6/2010 | Smith et al. | 600/114 |
| 2010/0174144 A1 | 7/2010 | Hsu | |
| 2010/0185056 A1 | 7/2010 | Gordon | |
| 2010/0187408 A1 | 7/2010 | Klem | |
| 2010/0201985 A1 | 8/2010 | Wang | |
| 2010/0204609 A1 | 8/2010 | Worth | |
| 2010/0217076 A1 | 8/2010 | Ratnakar | |
| 2010/0217081 A1 | 8/2010 | Deppmeier | |
| 2010/0228086 A1 | 9/2010 | Ohki | |
| 2010/0249496 A1 | 9/2010 | Cardenas | |
| 2010/0256447 A1 | 10/2010 | Dubi | |
| 2010/0286475 A1 | 11/2010 | Robertson | |
| 2010/0298640 A1 | 11/2010 | Oneda | |
| 2010/0298773 A1 | 11/2010 | Nitsan | |
| 2010/0305503 A1 | 12/2010 | Fang | |
| 2010/0317919 A1 | 12/2010 | Takaoka | |
| 2010/0317921 A1 | 12/2010 | Marple | |
| 2010/0318061 A1 | 12/2010 | Derrick | |
| 2011/0028790 A1 | 2/2011 | Farr | |
| 2011/0112363 A1 | 5/2011 | Koga | |
| 2011/0160530 A1 | 6/2011 | Ratnakar | |
| 2011/0184243 A1 | 7/2011 | Wright | |
| 2011/0196200 A1 | 8/2011 | Glozman | |
| 2011/0196204 A1 | 8/2011 | Setty | |
| 2011/0224487 A1 | 9/2011 | Ogawa | |
| 2011/0245600 A1 | 10/2011 | Ishii | |
| 2011/0245609 A1 | 10/2011 | Laser | |
| 2011/0257478 A1 | 10/2011 | Kleiner | |
| 2011/0263938 A1 | 10/2011 | Levy | |
| 2011/0282144 A1 | 11/2011 | Gettman | |
| 2011/0282148 A1 | 11/2011 | Kase | |
| 2011/0288374 A1 | 11/2011 | Hadani | |

(56) References Cited

U.S. PATENT DOCUMENTS

| | | |
|---|---|---|
| 2011/0295061 A1 | 12/2011 | Haramaty |
| 2011/0295062 A1 | 12/2011 | GratacosSolsona |
| 2011/0295064 A1 | 12/2011 | Kagawa |
| 2011/0306832 A1 | 12/2011 | Bassan |
| 2011/0313249 A1 | 12/2011 | Viola |
| 2012/0010465 A1 | 1/2012 | Erikawa |
| 2012/0029291 A1 | 2/2012 | Wallace |
| 2012/0040305 A1 | 2/2012 | Karazivan |
| 2012/0041534 A1 | 2/2012 | Clerc |
| 2012/0046524 A1 | 2/2012 | Miyamoto |
| 2012/0053407 A1 | 3/2012 | Levy |
| 2012/0065468 A1 | 3/2012 | Levy |
| 2012/0071748 A1 | 3/2012 | Mark |
| 2012/0078042 A1 | 3/2012 | Uram |
| 2012/0088965 A1 | 4/2012 | Stokes |
| 2012/0104230 A1 | 5/2012 | Eismann |
| 2012/0178995 A1 | 7/2012 | Newton |
| 2012/0209062 A1 | 8/2012 | Qiao |
| 2012/0229615 A1 | 9/2012 | Kirma |
| 2012/0232340 A1 | 9/2012 | Levy |
| 2012/0232342 A1 | 9/2012 | Reydel |
| 2012/0232343 A1 | 9/2012 | Levy |
| 2012/0253121 A1 | 10/2012 | Kitano |
| 2012/0253284 A1 | 10/2012 | Nitsan |
| 2012/0259175 A1 | 10/2012 | Reydel |
| 2012/0265094 A1 | 10/2012 | Goldfarb |
| 2013/0012778 A1 | 1/2013 | Bayer |
| 2013/0012794 A1 | 1/2013 | Zeng |
| 2013/0060086 A1 | 3/2013 | Talbert |
| 2013/0109916 A1 | 5/2013 | Levy |
| 2013/0109918 A1 | 5/2013 | Pagan |
| 2013/0110003 A1 | 5/2013 | Surti |
| 2013/0131445 A1 | 5/2013 | Zerfas |
| 2013/0131447 A1 | 5/2013 | Benning |
| 2013/0131454 A1 | 5/2013 | McCormack |
| 2013/0172670 A1 | 7/2013 | Levy |
| 2013/0172673 A1 | 7/2013 | Kennedy |
| 2013/0172674 A1 | 7/2013 | Kennedy |
| 2013/0172677 A1 | 7/2013 | Kennedy |
| 2013/0172678 A1 | 7/2013 | Kennedy |
| 2013/0190561 A1 | 7/2013 | Oskin |
| 2013/0194404 A1 | 8/2013 | Christiansen |
| 2013/0204088 A1 | 8/2013 | Miyamoto |
| 2013/0253272 A1 | 9/2013 | Takahashi |
| 2013/0314521 A1 | 11/2013 | Satake |

FOREIGN PATENT DOCUMENTS

| | | | |
|---|---|---|---|
| EP | 0029555 A2 | 6/1981 | |
| EP | 543738 A1 | 5/1993 | |
| EP | 730844 | 9/1996 | |
| EP | 1195630 A2 | 4/2002 | |
| EP | 1325458 | 7/2003 | |
| EP | 1347702 A2 | 10/2003 | |
| EP | 948283 B1 | 4/2004 | |
| EP | 1073365 B1 | 7/2005 | |
| EP | 1627595 A1 | 2/2006 | |
| EP | 668738 B1 | 6/2006 | |
| EP | 1472972 B1 | 10/2006 | |
| EP | 1790280 A1 | 5/2007 | |
| EP | 1834572 A1 | 9/2007 | |
| EP | 1952750 | 8/2008 | |
| EP | 1977682 A2 | 10/2008 | |
| EP | 1974000653 | 10/2008 | |
| EP | 1992292 A1 | 11/2008 | |
| EP | 2022389 A1 | 2/2009 | |
| EP | 2144571 A2 | 1/2010 | |
| EP | 2276389 A1 | 1/2011 | |
| EP | 1835847 B1 | 5/2011 | |
| EP | 1870014 B1 | 1/2012 | |
| EP | 2501271 A1 | 9/2012 | |
| EP | 2503933 A1 | 10/2012 | |
| EP | 2512577 A2 | 10/2012 | |
| EP | 2529660 A1 | 12/2012 | |
| EP | 2596756 A1 | 5/2013 | |
| EP | 2623019 A1 | 8/2013 | |
| GB | 2352922 A | 2/2001 | |
| JP | 55078932 | 6/1980 | |
| JP | 61055657 | 11/1986 | |
| JP | 5049000594 | 3/1993 | |
| JP | 6105000800 | 4/1994 | |
| JP | 7000000352 | 1/1995 | |
| JP | 8122000657 | 5/1996 | |
| JP | 1013007179 | 4/1998 | |
| JP | 1015001113 | 6/1998 | |
| JP | 11137512 | 5/1999 | |
| JP | 1116009340 | 6/1999 | |
| JP | 1116009341 | 6/1999 | |
| JP | 2000171727 A | 6/2000 | |
| JP | 2001061762 | 3/2001 | |
| JP | 2001198086 | 7/2001 | |
| JP | 2002000559 | 1/2002 | |
| JP | 2002058636 | 2/2002 | |
| JP | 2002065575 | 3/2002 | |
| JP | 2002078675 | 3/2002 | |
| JP | 2002216902 | 8/2002 | |
| JP | 2003038431 | 2/2003 | |
| JP | 2003061900 | 3/2003 | |
| JP | 2003111724 | 4/2003 | |
| JP | 2003190082 | 7/2003 | |
| JP | 2003220017 | 8/2003 | |
| JP | 2003245247 | 9/2003 | |
| JP | 2004022391 | 1/2004 | |
| JP | 2004049754 | 2/2004 | |
| JP | 2004049756 | 2/2004 | |
| JP | 2004129834 | 4/2004 | |
| JP | 2005013557 A | 1/2005 | |
| JP | 2005058547 | 3/2005 | |
| JP | 2005253543 | 9/2005 | |
| JP | 2006068109 A | 3/2006 | |
| JP | 2006218155 | 8/2006 | |
| JP | 2007020866 A | 2/2007 | |
| JP | 2007185276 | 7/2007 | |
| JP | 2008161569 A | 7/2008 | |
| JP | 2008229204 | 10/2008 | |
| JP | 2009233186 | 10/2009 | |
| JP | 2010178766 A * | 8/2010 | ............... A61B 1/00 |
| WO | 9219148 A1 | 11/1992 | |
| WO | 0052643 A1 | 9/2000 | |
| WO | 0245595 | 6/2002 | |
| WO | 2004026125 | 4/2004 | |
| WO | 2005082228 A1 | 9/2005 | |
| WO | 2006105932 A1 | 10/2006 | |
| WO | 2007113801 A2 | 10/2007 | |
| WO | 2007136859 A2 | 11/2007 | |
| WO | 2008012813 A1 | 1/2008 | |
| WO | 2008073243 | 6/2008 | |
| WO | 2008093288 | 8/2008 | |
| WO | 2008155776 | 12/2008 | |
| WO | 2008156623 | 12/2008 | |
| WO | 2009009414 | 1/2009 | |
| WO | 2009025843 | 2/2009 | |
| WO | 2009040744 | 4/2009 | |
| WO | 2009095915 | 8/2009 | |
| WO | 2010028612 | 3/2010 | |
| WO | 2010045406 | 4/2010 | |
| WO | 2010146587 A1 | 12/2010 | |
| WO | 2011008922 | 1/2011 | |
| WO | 2011083451 | 7/2011 | |
| WO | 2011126812 | 10/2011 | |
| WO | 2012038958 | 3/2012 | |
| WO | 2012056453 | 5/2012 | |
| WO | 2012077116 | 6/2012 | |
| WO | 2012077117 | 6/2012 | |
| WO | 2012088201 A2 | 6/2012 | |
| WO | 2012103266 | 8/2012 | |
| WO | 2012120507 | 9/2012 | |
| WO | 2012153324 | 11/2012 | |
| WO | 2013014673 | 1/2013 | |
| WO | 2013024476 | 2/2013 | |
| WO | 2013043704 | 3/2013 | |
| WO | 2013128136 | 9/2013 | |

(56) References Cited

FOREIGN PATENT DOCUMENTS

| WO | 2013131578 | 9/2013 |
|---|---|---|
| WO | 2013144944 | 10/2013 |
| WO | 2014061023 | 4/2014 |

OTHER PUBLICATIONS

First Image of an Endo Smart Cap, made by Medivators, and obtained from http://www.bymemedical.com/prod/145L.jpg and advertised at http://www.medivators.com/products/endoscopy-procedure-products/irrigation-tubing/endo-smartcap%C2%AE.

Second Image of an Endo Smart Cap, made by Medivators, and obtained from http://www.bymemedical.com/prod/150L.jpg and advertised at http://www.medivators.com/products/endoscopy-procedure-products/irrigation-tubing/endo-smartcap%C2%AE.

Brochure for US Endoscopy's AquaShield Water Bottle System, 2010.

International Search Report for PCT/IL2012/050299, Nov. 15, 2012.
International Search Report for PCT/IL2012/050274, Nov. 15, 2012.
International Search Report for PCT/IL2013/050840, Feb. 2, 2014.
International Search Report for PCT/IL2012/050037, Jun. 1, 2012.
International Search Report for PCT/IL2011/050050, May 16, 2012.
International Search Report for PCT/IL2011/050049, May 15, 2012.
International Search Report for PCT/IL2011/000832, May 16, 2012.
International Search Report of PCT/IL2011/000745, dated May 8, 2012.

* cited by examiner

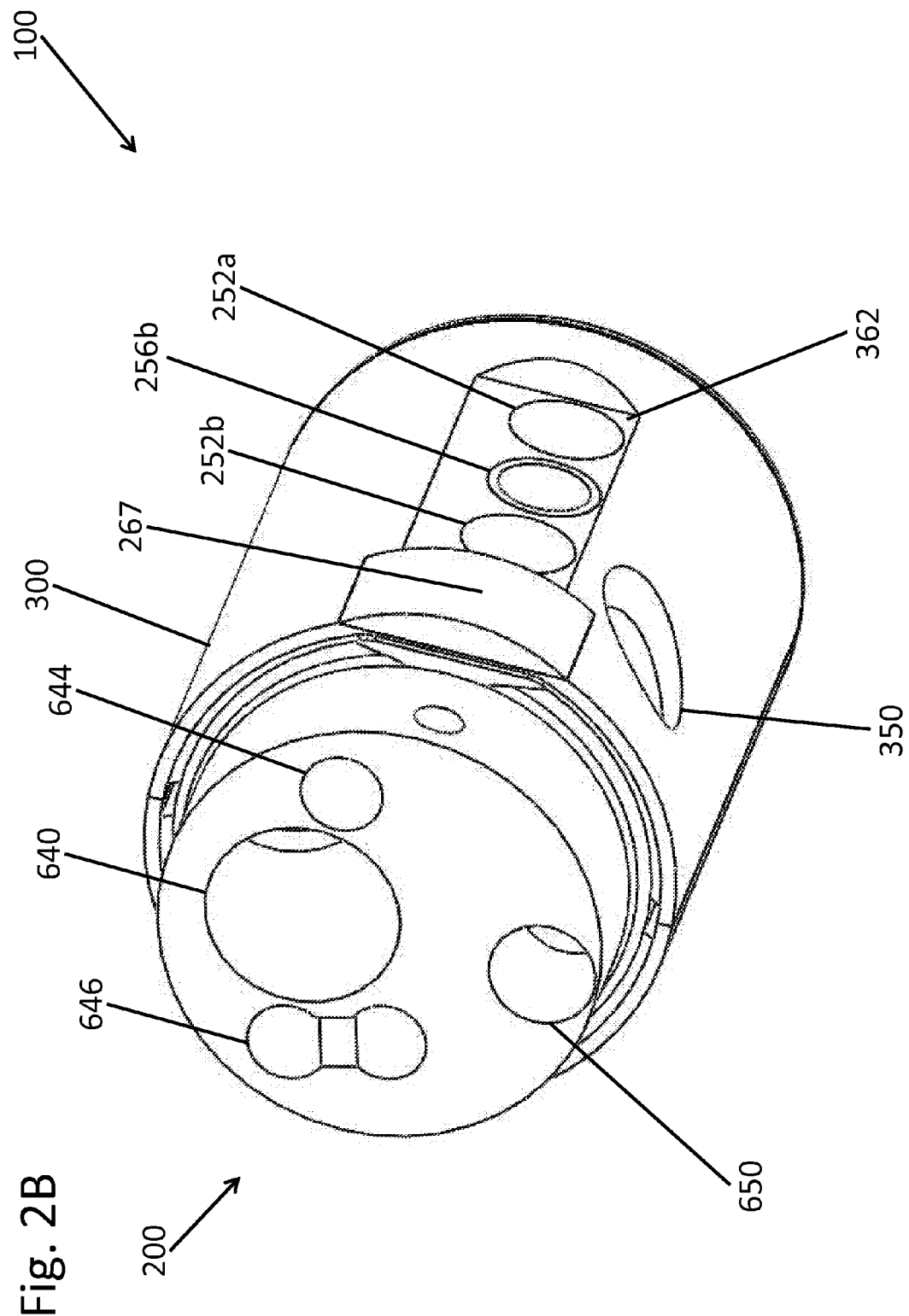

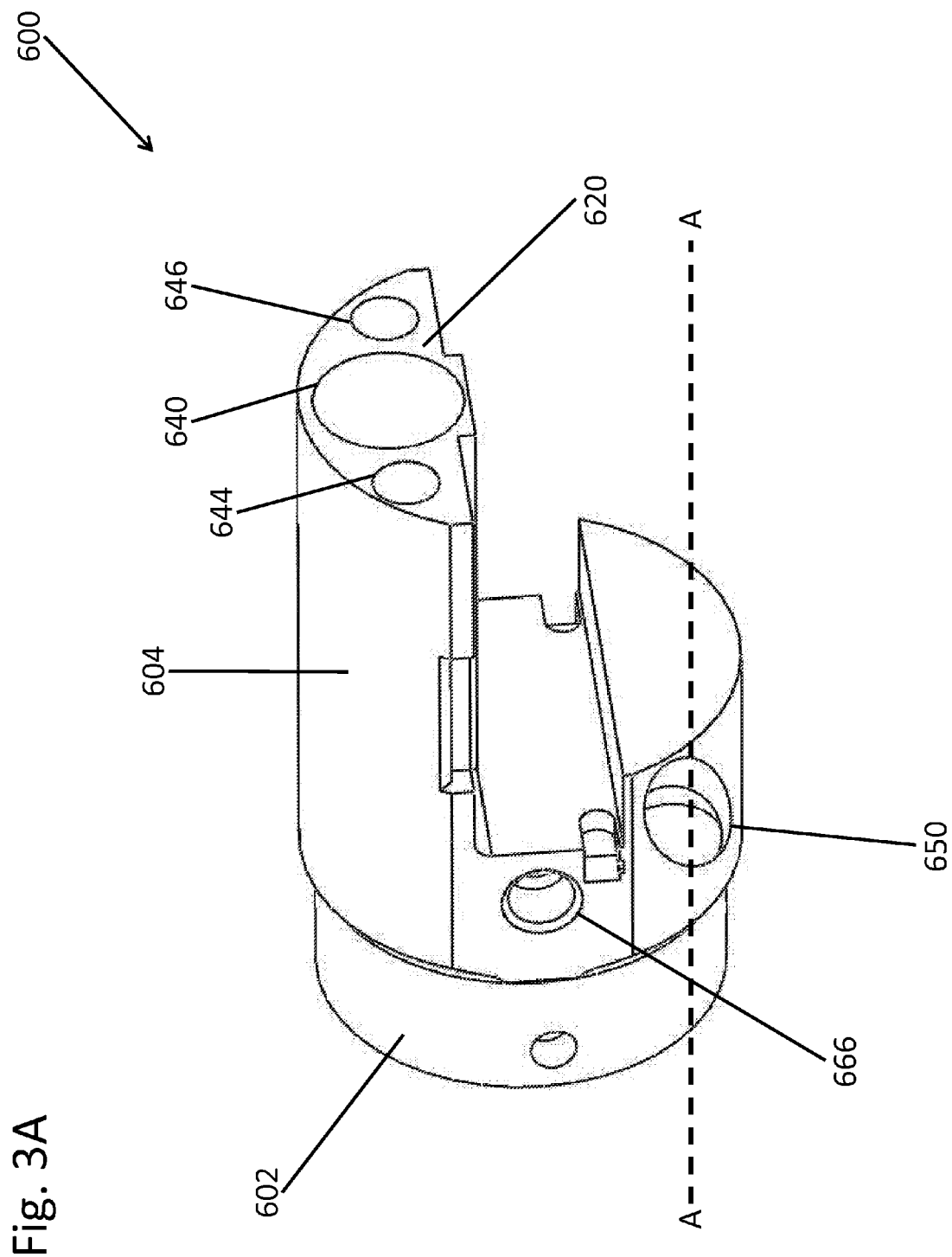

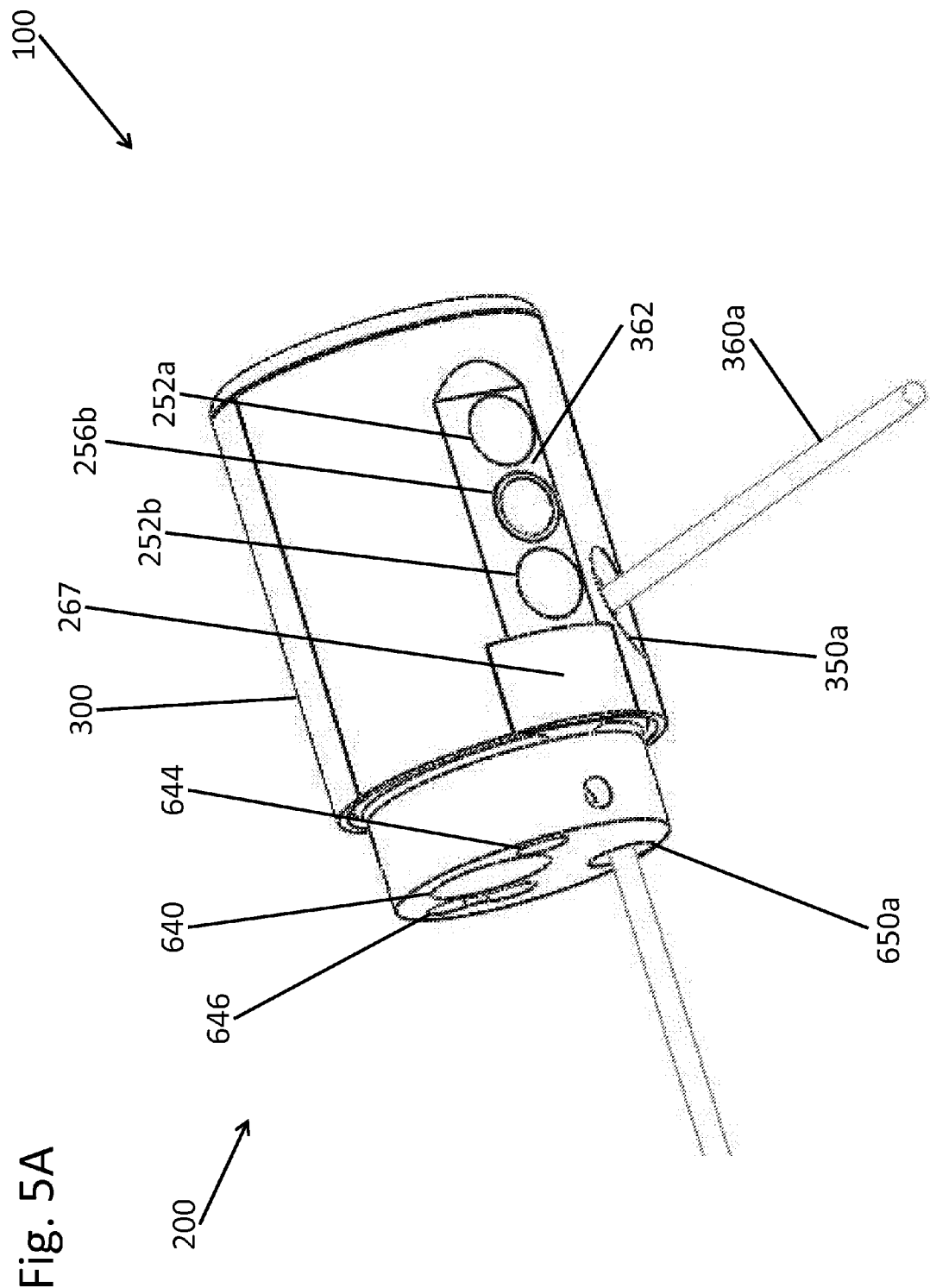

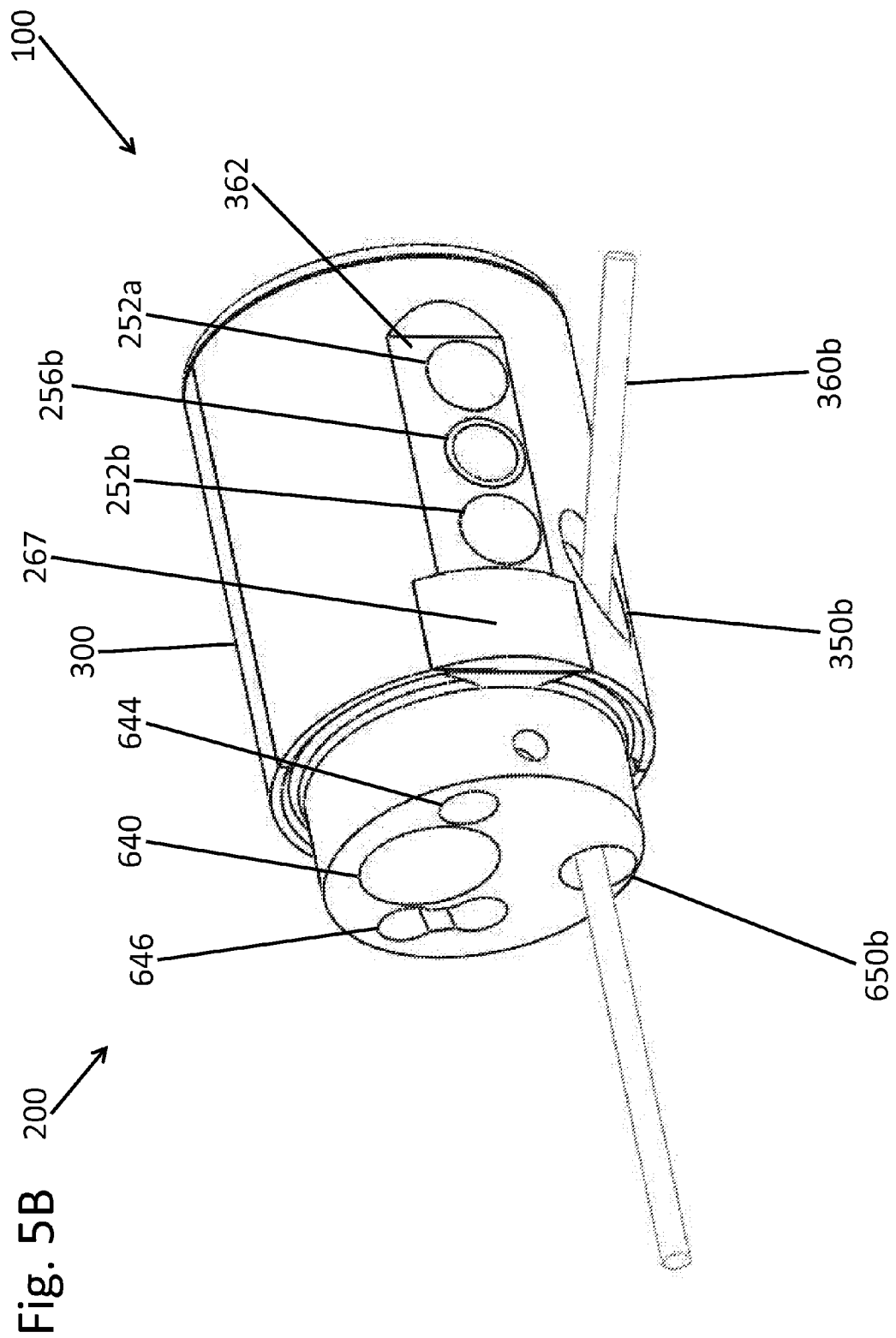

MULTI CAMERA ENDOSCOPE HAVING A SIDE SERVICE CHANNEL

REFERENCE TO CO-PENDING APPLICATIONS

Priority is claimed to U.S. Provisional Patent application Ser. No. 61/449,743, filed on Mar. 7, 2011.

FIELD OF THE INVENTION

Embodiments of the disclosure relate to a multi camera endoscope assembly having one or more side service channels.

BACKGROUND

Endoscopes have attained great acceptance within the medical community, since they provide a means for performing procedures with minimal patient trauma, while enabling the physician to view the internal anatomy of the patient. Over the years, numerous endoscopes have been developed and categorized according to specific applications, such as cystoscopy, colonoscopy, laparoscopy, upper GI endoscopy and others. Endoscopes may be inserted into the body's natural orifices or through an incision in the skin.

An endoscope is usually an elongated tubular shaft, rigid or flexible, having a video camera or a fiber optic lens assembly at its distal end. The shaft is connected to a handle, which sometimes includes an ocular for direct viewing. Viewing is also usually possible via an external screen. Various surgical tools may be inserted through a working channel in the endoscope for performing different surgical procedures.

Endoscopes, such as colonoscopes, that are currently being used, typically have a front camera for viewing the internal organ, such as the colon, an illuminator, a fluid injector for cleaning the camera lens and sometimes also the illuminator and a working channel for insertion of surgical tools, for example, for removing polyps found in the colon. Often, endoscopes also have fluid injectors ("jet") for cleaning a body cavity, such as the colon, into which they are inserted. The illuminators commonly used are fiber optics which transmit light, generated remotely, to the endoscope tip section. The use of light-emitting diodes (LEDs) for illumination is also known.

Among the disadvantages of such endoscopes, are their limited field of view and their limited options for operating medical and surgical tools.

There is thus a need in the art for endoscopes, such as colonoscopies, that allow a broader field of view and allow extended access of surgical tools as well as enabling efficient packing of all necessary elements in the tip section, while maintaining their function.

SUMMARY

The following embodiments and aspects thereof are described and illustrated in conjunction with systems, tools and methods, which are meant to be exemplary and illustrative, not limiting in scope.

There is provided herein, according to some embodiments of the invention a tip section of an endoscope, the tip section comprising: at least one front-pointing camera and at least one front illuminator associated therewith; at least one side-pointing camera and at least one of side illuminator associated therewith; a front working channel configured for insertion of a medical tool; and a side service channel configured for insertion of a medical tool.

In some embodiments, the tip section further comprises at least one front fluid injector configured for cleaning at least one of the front-pointing camera and at least one of the front illuminator.

In some embodiments, the tip section further comprises at least one side fluid injector configured for cleaning at least one of the side-pointing camera and at least one of the side illuminator.

In some embodiments, the tip section further comprises a pathway fluid injector for inflating and/or cleaning a body cavity into which the endoscope is inserted.

In some embodiments, the tip section comprises two side-pointing cameras.

In some embodiments, each of the side-pointing cameras is directed to opposing sides.

In some embodiments, each of the side-pointing cameras is essentially perpendicular to the front camera surface.

In some embodiments, the at least one side-pointing camera forms an obtuse angle with the front camera surface.

In some embodiments, the at least one side-pointing camera forms an acute angle with the front camera surface.

In some embodiments, the side service channel is curved at an angle of about 90° relative to the long dimension of the tip section towards a side wall of the tip section.

In some embodiments, the side service channel is curved at an obtuse angle relative to the long dimension of the assembly, towards a side wall of the tip section.

In some embodiments, the side service channel is curved at an acute angle relative to the long dimension of the assembly, towards a side wall of the tip section.

In some embodiments, the front working channel is further configured for insertion of a cleaning fluid and the side service channel is configured for suctioning the cleaning fluid.

In some embodiments, the side service channel is further configured for insertion of a cleaning fluid and the front working channel is configured for suctioning the cleaning fluid.

In some embodiments, the tip section comprises two side service channels directed essentially to opposing sides of the tip section.

In some embodiments, the side service channel comprises a proximal section, which splits into two distal sections directed essentially to opposing sides of the tip section.

In some embodiments, each one of the two distal sections is curved at an angle of about 90° relative to the long dimension of the tip section towards a side wall of the tip section.

In some embodiments, each one of the two distal sections is curved at an obtuse angle relative to the long dimension of the tip section towards a side wall of the tip section.

In some embodiments, each one of the two distal sections is curved at an acute angle relative to the long dimension of the tip section towards a side wall of the tip section.

In some embodiments, at least one of the front and side illuminators comprises at least one discrete illuminator.

In some embodiments, each of the front and side illuminators comprises a light-emitting diode (LED).

In some embodiments, at least one of the front and side illuminators is configured to emit white light.

In some embodiments, at least one of the front and side illuminators is configured to emit ultraviolet light.

In some embodiments, at least one of the front and side illuminators is configured to emit infrared light.

In some embodiments, at least one of the front and side illuminators is configured to emit near-infrared light.

In some embodiments, the front and side illuminators are configured to emit light in different wavelengths.

In some embodiments, each of the front-pointing camera and the side-pointing camera comprises an image sensor such as, but not limited to, a Charge Coupled Device (CCD) or a Complementary Metal Oxide Semiconductor (CMOS).

In some embodiments, the front and side fluid injectors are connected to a same fluid supply channel.

In some embodiments, the endoscope is a colonoscope.

In some embodiments, the endoscope is a flexible endoscope.

In some embodiments, the endoscope is a gastroscope.

In some embodiments, fields of view of the front-pointing camera and side-pointing camera are at least partially overlapping.

In some embodiments, at least one of the front and side cameras comprises a lens assembly providing a field of view of 90 degrees or more.

In some embodiments, at least one of the front and side cameras comprises a lens assembly providing a field of view of 120 degrees or more.

In some embodiments, at least one of the front and side cameras comprises a lens assembly providing a focal length of approximately 3-100 millimeters.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. It is intended that the embodiments and figures disclosed herein are to be considered illustrative rather than restrictive. The figures are listed below.

FIG. 2B shows a perspective view of a tip section of an endoscope assembly according to some embodiments;

FIG. 3A shows a perspective view of a tip section of an endoscope assembly according to some embodiments;

FIG. 5A shows a perspective view of a fluid channeling component of an endoscope assembly with a medical tool inserted through a side service channel thereof, according to some embodiments; and FIG. 5B shows a perspective view of a fluid channeling component of an endoscope assembly with a medical tool inserted through a side service channel thereof, according to some embodiments.

DETAILED DESCRIPTION

Figure 1:
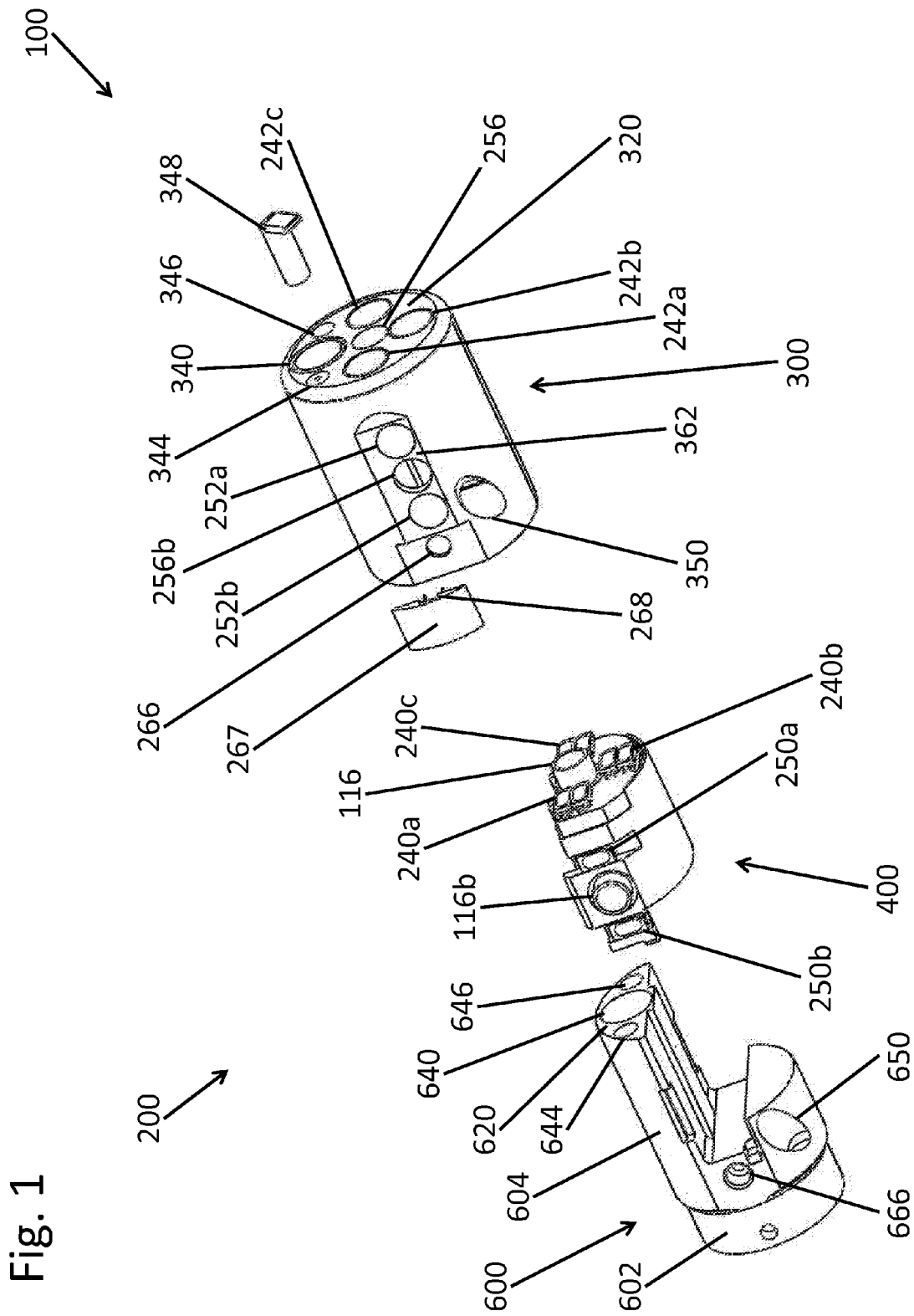
FIG. 1 shows an exploded view of a tip section of an endoscope assembly according to some embodiments.

Reference is now made to FIG. 1, which shows an exploded view of a tip section 200 of an endoscope assembly 100 according to an embodiment.

An aspect of some embodiments relates to endoscope assembly 100 having tip section 200 equipped with one or more side service channels.

It is noted that the term "endoscope" as mentioned to herein may refer particularly to a colonoscope, according to some embodiments, but is not limited only to colonoscopes. The term "endoscope" may refer to any instrument used to examine the interior of a hollow organ or cavity of the body.

Tip section 200 may be turnable by way of flexible shaft (not shown) which may also be referred to as a bending section, for example a vertebra mechanism.

According to an embodiment, tip section 200 of an endoscope may include a tip cover 300, an electronic circuit board assembly 400 and a fluid channeling component 600.

Electronic circuit board assembly 400 may be configured to carry a front looking camera 116 and side looking cameras 116a (not shown) and 116b which may be similar to front looking camera 116 and may include a Charge Coupled Device (CCD) or a Complementary Metal Oxide Semiconductor (CMOS) image sensor.

Electronic circuit board assembly 400 may be configured to carry front illuminators 240a, 240b, 240c, which may be associated with front looking camera 116, may be positioned to essentially illuminate front looking camera's 116 fields of view.

In addition, electronic circuit board assembly 400 may be configured to carry side illuminators 250a and 250b, which may be associated with side looking camera 116b, may be positioned to essentially illuminate side looking camera's 116b fields of view. Electronic circuit board assembly 400 may also be configured to carry side illuminators, which may be associated with side looking camera 116a (not shown), which may be similar to side illuminators 250a and 250b.

Front illuminators 240a, 240b, 240c and side illuminators 250a and 250b may optionally be discrete illuminators and may include a light-emitting diode (LED), which may be a white light LED, an infrared light LED, a near infrared light LED, an ultraviolet light LED or any other LED.

The term "discrete", concerning discrete illuminator, may refer to an illumination source, which generates light internally—in contrast to a non-discrete illuminator, which may be, for example, a fiber optic merely transmitting light generated remotely.

Figure 2A:
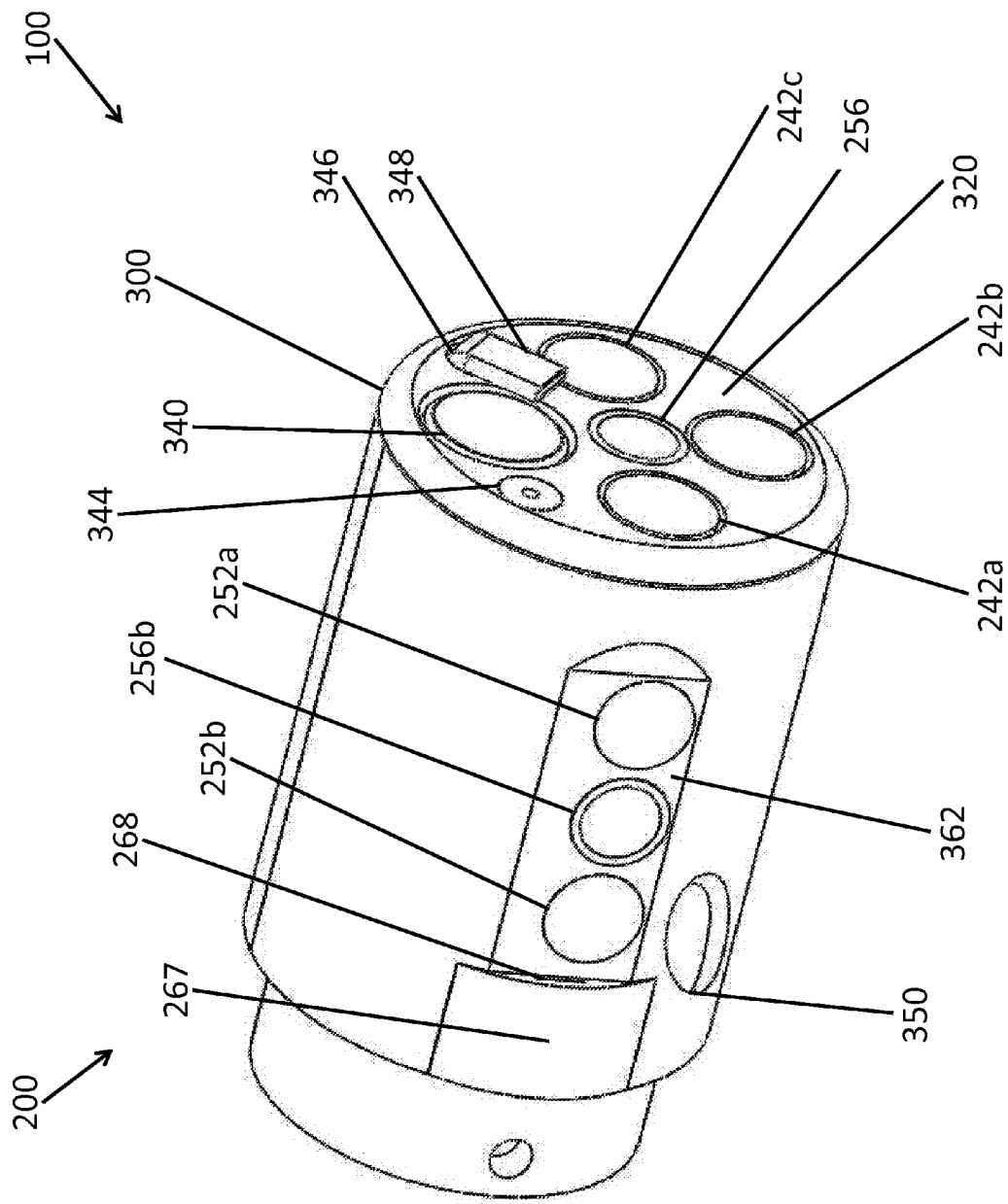
FIG. 2A shows a perspective view of a tip section of an endoscope assembly according to some embodiments.

Reference is now made to FIGS. 2 A and B, which shows a perspective view of a tip section 200 of an endoscope assembly 100 according to an embodiment.

Tip cover 300 may be configured to fit over the inner parts of the tip section 200 including electronic circuit board assembly 400 and fluid channeling component 600 and to provide protection to the internal components in the inner parts.

Tip cover 300 may include a front panel 320 having a front optical assembly 256, of front looking camera 116. Front optical assembly 256 may include a plurality of lenses, static or movable, which may provide a field of view of up to essentially 180 degrees. Front optical assembly 256 may provide a focal length of up to about 100 millimeters.

Optical axis of front looking camera 116 may be essentially directed along the long dimension of the endoscope. However, since front looking camera 116 is typically a wide angle camera, its field of view may include viewing directions at large angles to its optical axis. Additionally, front panel 320 may include optical windows 242a, 242b and 242c of illuminators 240a, 240b and 240c, respectively. It should be noted that number of illumination sources used for illumination of the field of view may vary.

In addition, front panel 320 may include a working channel opening 340 of a working channel 640, which is further discussed below.

Jet channel opening 344 of jet channel 644 may also be located on front panel 320 of tip cover 300. Jet channel 644 may be configured for providing high-pressure jet of fluid such as water or saline for cleaning the walls of the body cavity.

Also located on front panel 320 of tip cover 300 is injector opening 346 of injector channel 646 having a nozzle 348 aimed at front optical assembly 256. Injector channel 646 may be configured for injecting fluid (liquid and/or gas) to wash contaminants such as blood, feces and other debris from front optical assembly 256 of front looking camera 116. Optionally, injector channel 646 may be configured for cleaning front optical assembly 256 and one two or all of optical windows 242a, 242b and 242c. Injector channel 646 may be fed by fluid such as water and/or gas which may be used for cleaning and/or inflating a body cavity.

Visible on the sidewall 362 of tip cover 300 is side optical assembly 256b for side looking camera 116b, which may be similar to front optical assembly 256 and optical windows 252a and 252b of illuminators 250a and 250b for side looking camera 116b. Also on the sidewall 362 of tip cover 300 one the opposing side to side optical assembly 256b is an optical assembly (not shown) for side looking camera 116a (not shown), which may be similar to side optical assembly 256b and optical windows 252a and 252b of illuminators 250a and 250b for side looking camera 116b.

Optical axis of side looking camera 116b may be essentially directed perpendicular to the long dimension of the endoscope. Optical axis of side looking camera 116b is essentially directed perpendicular to the long dimension of the endoscope. However, since side looking camera 116b is typically a wide angle camera, its field of view may include viewing directions at large angles to its optical axis.

In addition, side injector opening 266 of side injector channel 666 may be located at distal end of sidewall 362. A nozzle cover 267 may be configured to fit side injector opening 266.

Additionally, nozzle cover 267 may include a nozzle 268 which may be aimed at side optical assembly 256b and configured for injecting fluid to wash contaminants such as blood, feces and other debris from side optical assembly 256b of side looking camera 116b. The fluid may include gas which may be used for inflating a body cavity. Optionally, nozzle 268 may be configured for cleaning both side optical assembly 256b and optical windows 252a and/or 252b.

According to some embodiments, side injector channel 666 may be configured to supply fluids for cleaning any of the tip elements (such as any optical assembly, windows, illuminators, and other elements).

Optionally, injector channel 646 and side injector channel 666 may be fed from same channel.

It is noted that according to some embodiments, although tip section 200 is presented herein showing one side thereof, the opposing side may include elements similar to the side elements described herein (for example, side looking camera, side optical assembly, injector(s), nozzle(s), illuminator(s), window(s), opening(s) and other elements).

Sidewall 362 may have a form of an essentially flat surface which assists in directing the cleaning fluid injected from injector channel 666 towards side optical assembly 256b and optical windows 252a and/or 252b. Lack of such flat surface may result in dripping of the cleaning fluid along the curved surface of tip section 200 of the endoscope without performing the desired cleaning action.

It is noted that according to some embodiments, tip section 200 may include more than one side looking cameras. In this case, the side looking cameras may be installed such that their field of views are substantially opposing. However, different configurations and number of side looking cameras are possible within the general scope of the current invention.

Fluid channeling component 600 includes a side service channel 650 having a side service channel opening 350. Side service channel 650, which will be discussed in more detail herein below, is configured to improve the performance of the endoscope (particularly, the colonoscope). Current colonoscopes typically have one working channel, which opens at the front distal section of the colonoscope. Such front working channel is adapted for insertion of a surgical tool. The physician is required to perform all necessary medical procedures, such as biopsy, polyp removal and other procedures, via this one channel. In addition, for treating (removing/biopsying) polyps or lesions found on the side walls of the colon, tip sections that have only a front working channel need to retracted and repositioned with their front facing the polyp or lesion. This re-positioning of the tip may result in "loosing" the polyp/lesion and further effort and time must be invested in re-locating it. These are major limitations that currently doctors have to face. According to some embodiments of this invention, there is provided herein an endoscope (such as colonoscope) that includes (in a tip section thereof), in addition to a front camera and one or more side cameras, and in addition to a front working channel, also a side service channel that is configured for insertion of a medical (such as a surgical) tool, optionally in addition to a medical tool inserted from the front working channel. The side service channel allows performance of medical procedures from (or in proximity to) the side of the tip section, while at the same time viewing the procedure by the side camera. This substantially increases the performance of the endoscope. Moreover, the front working channel and the side service channel may be used simultaneously for medical procedures. An example of such procedure may include cleaning of the colon. A common problem exists when doctors find out that the patient's colon is not sufficiently clean. In such cases, the doctor can try to clean the colon part using the "jet" exiting from the front part of the tip and in bad cases the doctor is forced to send the patient home and reschedule his/her appointment. According to embodiments of the invention, the two channels can be used simultaneously for cleaning. For example, a cleaning fluid (such as water or water with air) may be inserted through the front working channel and suctioned out from the side service channel, or vice versa. This may allow a better cleaning procedure that may solve or mitigate the problem of less efficient colonoscopies due to a non-cleaned colon.

In addition, a colonoscopy performed using a colonoscope according to embodiments of the invention may save the need of a cleaning procedure, currently performed by the patient him/herself, prior to colonoscopy.

Figure 3B:
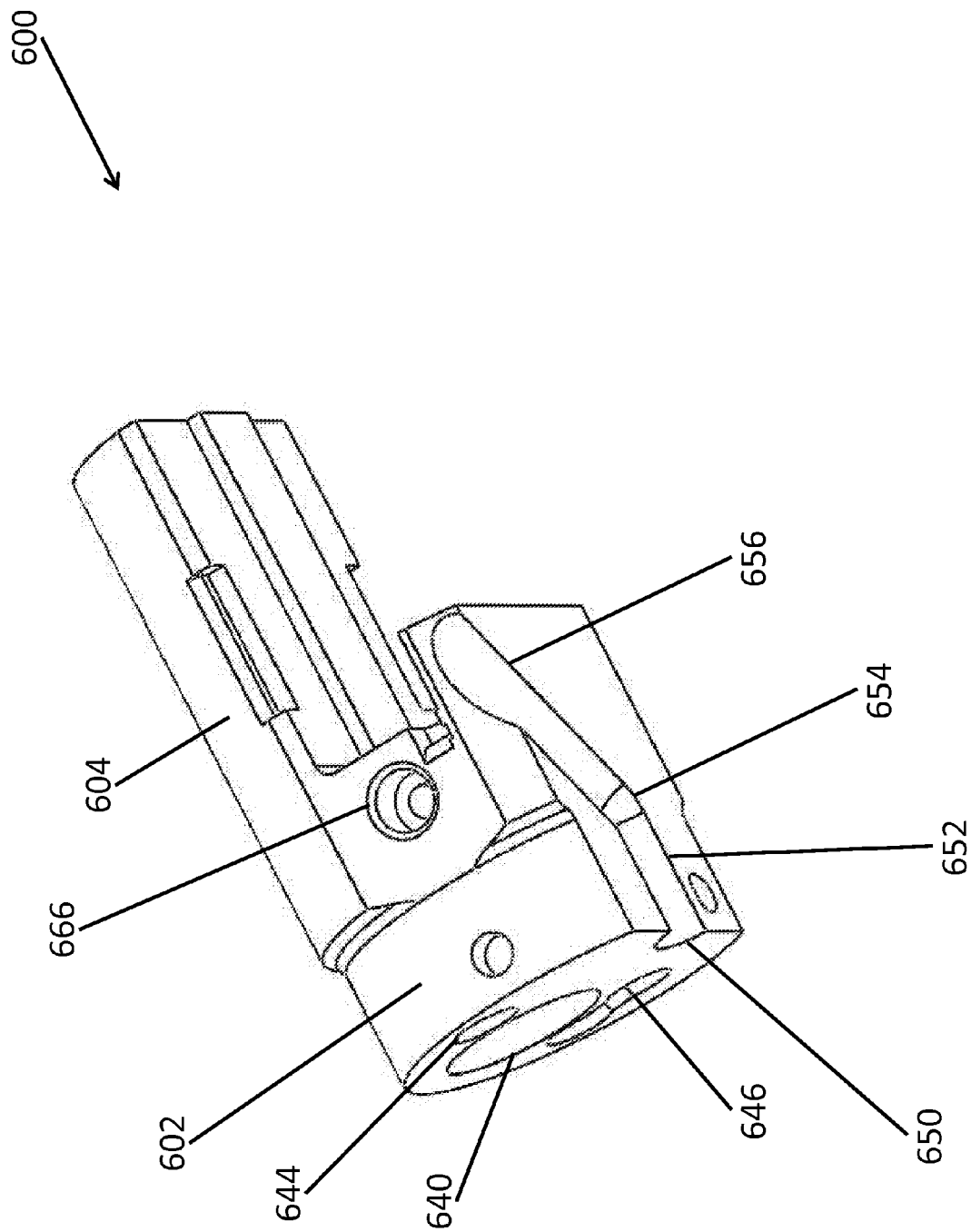
FIG. 3B shows a perspective view of a tip section of an endoscope assembly according to some embodiments.

Reference is now made to FIGS. 3A and 3B which show a perspective view of a fluid channeling component 600 of an endoscope assembly according to an embodiment.

According to some embodiments, fluid channeling component 600 may be configured as a separate component from electronic circuit board assembly 400. This configuration may be adapted to separate the fluid channels and working channel 640, which are located in fluid channeling component 600 from the sensitive electronic and optical parts which may be located in the area of electronic circuit board assembly 400.

According to some embodiments, fluid channeling component 600 may include a Proximal fluid channeling section 602 which may have an essentially cylindrical shape and a unitary distal channeling section 604. Distal fluid channeling section 604 may partially continue the cylindrical shape of proximal fluid channeling section 602 and may have a shape of a partial cylinder (optionally elongated partial cylinder). Distal fluid channeling section 604 may have only a fraction of the cylinder (along the height axis of the cylinder), wherein another fraction of the cylinder (along the height axis of the cylinder) is missing. Distal fluid channeling section 604 may be integrally formed as a unitary block with proximal fluid channeling section 602. The height of distal fluid channeling section 604 may by higher than that of proximal fluid channeling section 602. In the case of distal fluid channeling section 604, the shape of the partial cylinder (for example, partial cylinder having only a fraction of a cylinder shape along one side of the height axis) may provide a space to accommodate electronic circuit board assembly 400 (FIG. 1).

Distal fluid channeling section 604 may include a working channel 640, which may be configured for insertion of a surgical tool, for example, to remove, treat and/or extract a sample of the object of interest found in the colon or its entirety for biopsy.

Distal fluid channeling section 604 may further include a jet fluid channel 644 (depicted as jet fluid channel 744 in FIGS. 4A, 4B, and 4C) which may be configured for providing high pressure jet of fluid such as water or saline for cleaning the walls of the body cavity (such as the colon) and optionally for suction. Distal fluid channeling section 604 may further include injector channel 646 (depicted as injector channel 746 in FIGS. 4A, 4B, and 4C), which may be used for injecting fluid (liquid and/or gas) to wash contaminants such as blood, feces and other debris from front optical assembly 256 (FIG. 1) of forwards looking camera 116 (FIG. 1).

Proximal fluid channeling section 602 of fluid channeling component 600 may include a side injector channel 666 which may be connected to side injector opening 266 (FIG. 1).

Reference is now made back to FIG. 1. Tip section 200 may include a front-pointing camera 116 as well as side looking camera 116b. While front-pointing camera 116 may be able to detect objects of interest (such as a polyp or another pathology), based on its, side-pointing camera may be able to detect additional objects of interest which are normally hidden from the front-pointing camera 116.

Once an object of interest has been detected, endoscope operator may desire to insert a surgical tool and remove, treat and/or extract a sample of the polyp or its entirety for biopsy.

In some cases, objects of interest may only be visible through side looking camera 116b, in this case, it may be beneficial for the endoscope's operator to be able to use surgical tools, which can access the object of interest and perform surgical operations while the object of interest is visible by side looking camera 116b.

Reference is now made back to FIGS. 3A, 3B. Fluid channeling component 600 may include a side service channel 650 having a side service channel opening 350 (FIG. 1).

Side service channel 650 includes a proximal section 652, a curve 654 and a distal section 656 and is located within fluid channeling component 600.

Proximal section 652 of side service channel 650 is essentially directed along the long dimension of the endoscope.

Curve 654 of side service channel 650 is configured to connect proximal section 652 and distal section 656 and curve (at essentially a right angle) (90°) or in an obtuse angle) distal section 656 towards the side of fluid channeling component 600.

It is noted that according to some embodiments, a curve, such as curve 654 may be configured to create an acute angle between distal proximal section end 652 and a proximal distal section end 656.

Side service channel 650 may be configured to allow the endoscope operator to insert a surgical tool (not shown) and remove, treat and/or extract a sample of the object of interest or its entirety for biopsy.

Advantageously, side service channel 650 may allow greater flexibility to the endoscope operator and allow the insertion of extra surgical tools in addition to the surgical tools which may be inserted through working channel 640.

Figure 4A:
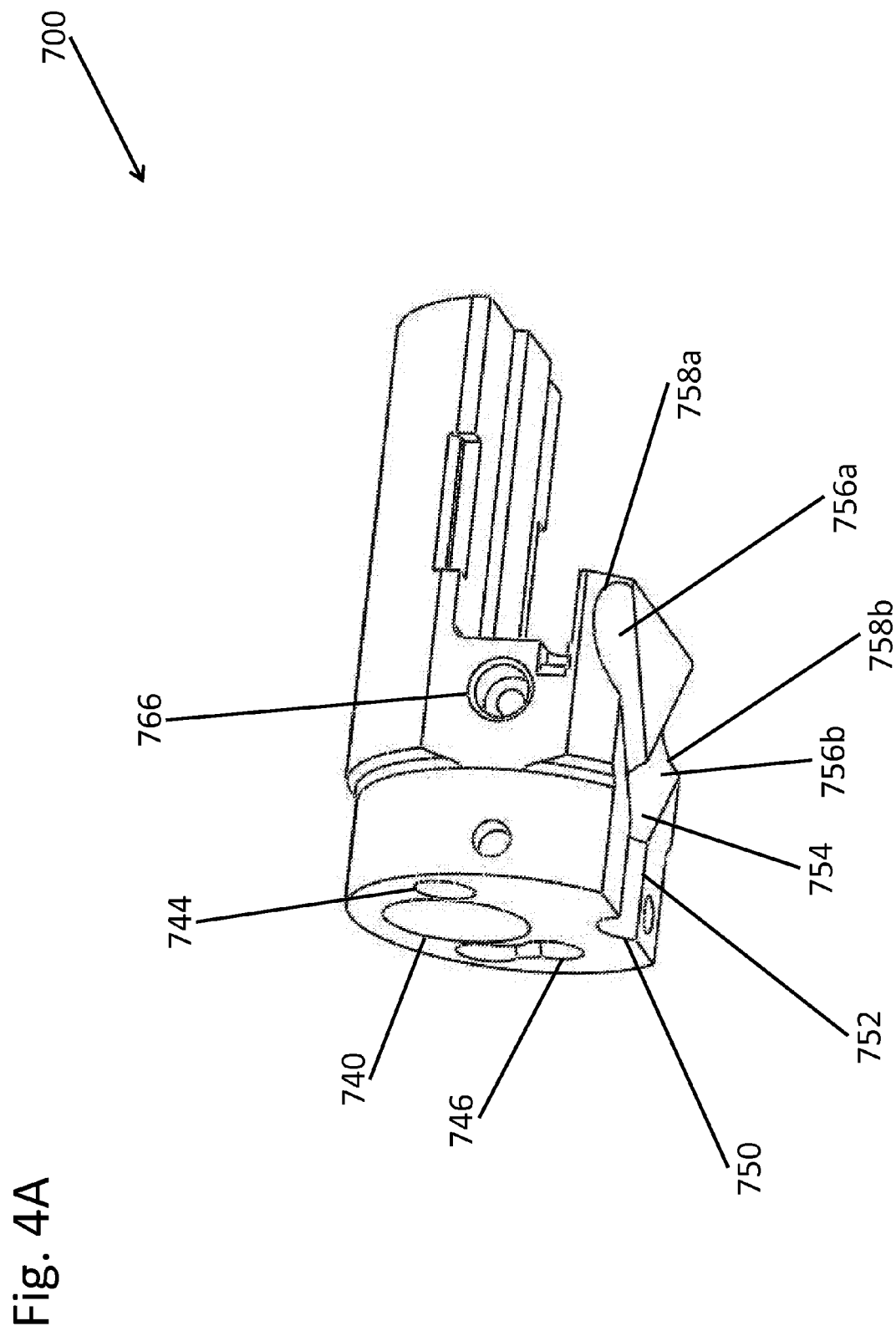
FIG. 4A shows a perspective view of a tip section of an endoscope assembly according to some embodiments.
Figure 4B:
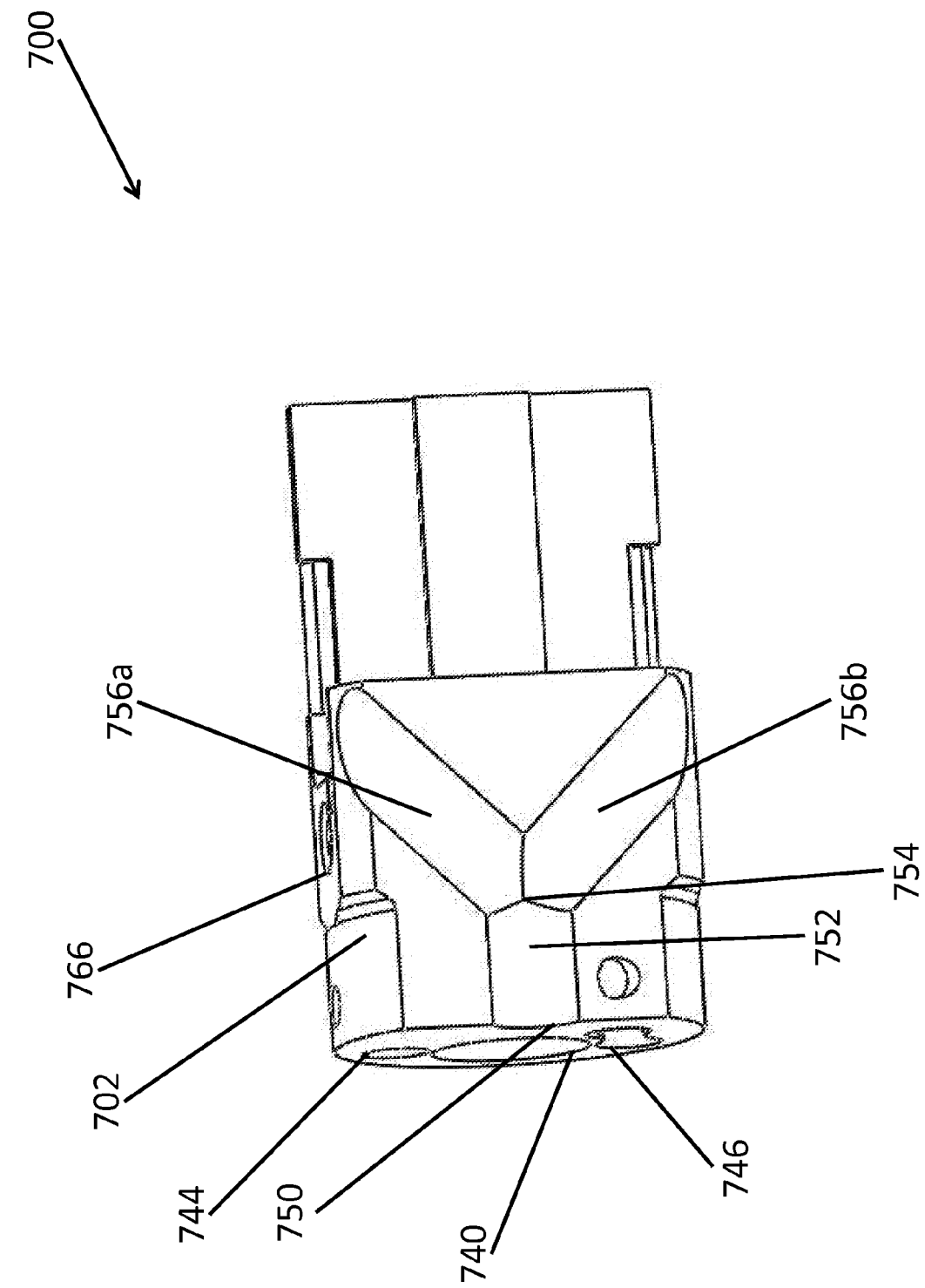
FIG. 4B shows a perspective view of a tip section of an endoscope assembly according to some embodiments.
Figure 4C:
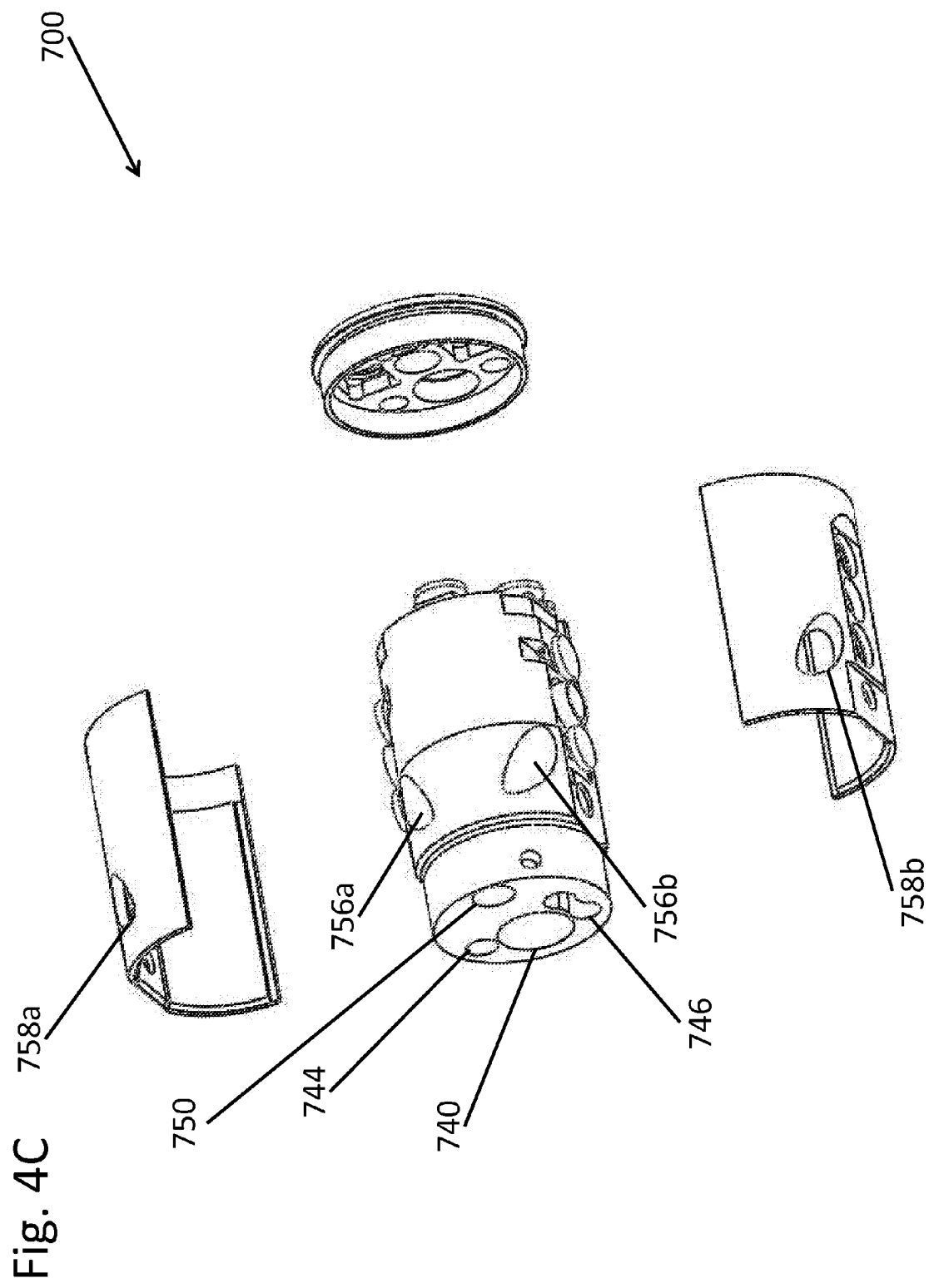
FIG. 4C shows a perspective view of a tip section of an endoscope assembly according to some embodiments.

Reference is now made to FIGS. 4A, 4B, and 4C, which show a perspective view of a fluid channeling component 700 of an endoscope assembly according to an embodiment.

According to some embodiments, fluid channeling component 700 may include a side service channel 750 having two side service channel openings 758a and 758b.

Side service channel 750 may be located within fluid channeling component 700 and may include a distal section 752, a split 754 and two distal sections 756a and 756b.

Proximal section 752 of side service channel 750 may be essentially directed along the long dimension of the endoscope.

Split 754 of side service channel 750 may be configured to split Proximal section 752 into two distal sections 756a and 756b and divert distal sections 756a and 756b towards two essentially opposite sides of fluid channeling component 700.

Side service channel 750 may be configured to allow the endoscope operator to insert a surgical tool (not shown) and remove, treat and/or extract a sample of the object of interest or its entirety for biopsy.

Advantageously, side service channel 750 may allow greater flexibility to the endoscope operator and allow the insertion of extra surgical tools in addition to the surgical tools, which may be inserted through working channel 740.

While some objects of interest may be visible and/or accessible via the endoscope front panel 320 (FIG. 1), some objects of interest may be more visible via side looking camera 116b (FIG. 1) and/or accessible via endoscope side service channel 750. Therefore, side service channel 750 may reduce the need to turn the tip section 200 towards the object of interest. Furthermore, side service channel 750 may allow the endoscope operator to access objects of interest, and perform surgical operations while object of interest is still visible by one of side looking camera 116b or 116c (FIG. 1).

Reference is now made to FIGS. 5A, 5B, which show a perspective view of a tip section of an endoscope assembly with a medical tool inserted through a side service channel thereof, according to some embodiments.

FIG. 5A shows tip section 200 of endoscope assembly 100, having side service channel 650 through which medical tool 360a is threaded and exits from side service channel opening 350a at essentially a right (90°) angle.

FIG. 5B shows tip section 200 of endoscope assembly 100, having side service channel 650 through which medical tool 360b is threaded and exits from side service channel opening 350b at an obtuse angle.

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

In the description and claims of the application, each of the words "comprise" "include" and "have", and forms thereof, are not necessarily limited to members in a list with which the words may be associated.

What is claimed is:

1. A tip section of an endoscope, the tip section comprising:
   a substantially cylindrical fluid channeling component having a proximal section, a first fraction, a second fraction and a third fraction,
   the proximal section comprises an auxiliary channel that divides into a first side service channel and a second side service channel, said proximal section having a distal end face;
   the first fraction comprises a housing that extends distally from the distal end face of the proximal section, said housing having exit openings for the first and second side service channels proximal to a distal end of the housing of the first fraction, said exit openings disposed on opposing sides of the fluid channeling component
   the third fraction comprises a housing that extends distally from the distal end face of the proximal section and encases a working channel therein;
   the second fraction comprises a void distal to the distal end face of the proximal section, said void prevents the first and third fractions from contacting each other;
   an electrical assembly configured to fit within said second fraction, wherein the electrical assembly comprises at least one front-pointing camera, at least one front illuminator and an integrated circuit board having mounted thereon at least one side-pointing camera; and
   a tip cover section configured to be removably attachable to said fluid channeling component and configured to receive said electrical assembly, wherein the tip section comprises a front working channel configured to mate to said working channel of the fluid channeling component and provide a contiguous pathway for receiving a medical tool.

2. The tip section of an endoscope according to claim 1, further comprising at least one front fluid injector configured for cleaning at least one of said front-pointing camera and at least one of said front illuminator.

3. The tip section of an endoscope according to claim 1, further comprising a side illuminator and at least one side fluid injector configured for cleaning at least one of said side-pointing camera and said side illuminator.

4. The tip section of an endoscope according to claim 1, further comprising a pathway fluid injector for inflating and/or cleaning a body cavity into which the endoscope is inserted.

5. The tip section of an endoscope according to claim 1, wherein said tip section comprises two side-pointing cameras.

6. The tip section of an endoscope according to claim 5, wherein each of said side-pointing cameras is directed to opposing sides.

7. The tip section of an endoscope according to claim 5, wherein each of said side-pointing cameras is essentially perpendicular to a surface of said front camera.

8. The tip section of an endoscope according to claim 5, wherein said at least one side-pointing camera forms an obtuse angle with a surface of said front camera.

9. The tip section of an endoscope according to claim 5, wherein said at least one side-pointing camera forms an acute angle with a surface of said front camera.

10. The tip section of an endoscope according to claim 1, wherein at least one of the first and second side service channels is curved at an angle of about 90 degrees relative to a long dimension of said tip section towards a side wall of said tip section.

11. The tip section of an endoscope according to claim 1, wherein at least one of the first and second service channels is curved at an obtuse angle relative to a long dimension of said tip section towards a side wall of said tip section.

12. The tip section of an endoscope according to claim 1, wherein at least one of the first and second service channels is curved at an acute angle relative to a long dimension of said tip section towards a side wall of said tip section.

13. The tip section of an endoscope according to claim 1, wherein said front working channel is further configured for insertion of a cleaning fluid and wherein at least one of the first and second side service channels is configured for suctioning said cleaning fluid.

14. The tip section of an endoscope according to claim 1, wherein at least one of the first and second side service channels is further configured for insertion of a cleaning fluid and wherein said front working channel is configured for suctioning said cleaning fluid.

15. The tip section of an endoscope according to claim 1, wherein at least one of the first and second side service channels comprises a proximal section which splits into two distal sections directed essentially to opposing sides of said tip section.

16. The tip section of an endoscope according to claim 15, wherein each one of said two distal sections is curved at an angle of about 90 degrees relative to a long dimension of said tip section towards a side wall of said tip section.

17. The tip section of an endoscope according to claim 15, wherein each one of said two distal sections is curved at an obtuse angle relative to a long dimension of said tip section towards a side wall of said tip section.

18. The tip section of an endoscope according to claim 15, wherein each one of said two distal sections is curved at an acute angle relative to a long dimension of said tip section towards a side wall of said tip section.

19. The tip section of an endoscope according to claim 1, further comprising at least one side illuminator and wherein at least one of said front and side illuminators comprises at least one discrete illuminator.

20. The tip section of an endoscope according to claim 19, wherein each of said front and side illuminators comprises a light-emitting diode (LED).

21. The tip section of an endoscope according to claim 1, further comprising at least one side illuminator and wherein at least one of said front and side illuminators is configured to emit white light.

22. The tip section of an endoscope according to claim 1, further comprising at least one side illuminator and wherein at least one of said front and side illuminators is configured to emit ultraviolet light.

23. The tip section of an endoscope according to claim 1, further comprising at least one side illuminator and wherein at least one of said front and side illuminators is configured to emit infrared light.

24. The tip section of an endoscope according to claim 1, further comprising at least one side illuminator and wherein at least one of said front and side illuminators is configured to emit near-infrared light.

25. The tip section of an endoscope according to claim 1, further comprising at least one side illuminator and wherein at least one of said front and side illuminators is configured to emit light in different wavelengths.

26. The tip section of an endoscope according to claim 1, wherein each of said front-pointing camera and said side-pointing camera comprises an image sensor.

27. The tip section of an endoscope according to claim 1 further comprising a front fluid injector and a side fluid injector connected to a same fluid supply channel.

28. The tip section of an endoscope according to claim 1, wherein said endoscope is a colonoscope.

29. The tip section of an endoscope according to claim 1, wherein said endoscope is a flexible endoscope.

30. The tip section of an endoscope according to claim 1, wherein said endoscope is a gastroscope.

31. The tip section of an endoscope according to claim 1, wherein fields of view of said front-pointing camera and side-pointing camera are at least partially overlapping.

32. The tip section of an endoscope according to claim 1, wherein at least one of said front and side cameras comprises a lens assembly providing a field of view of 90 degrees or more.

33. The tip section of an endoscope according to claim 1, wherein at least one of said front and side cameras comprises a lens assembly providing a field of view of 120 degrees or more.

34. The tip section of an endoscope according to claim 1, wherein at least one of said front and side cameras comprises a lens assembly providing a focal length of approximately 3-100 millimeters.

* * * * *